(12) United States Patent
Knauer et al.

(10) Patent No.: US 11,466,050 B2
(45) Date of Patent: Oct. 11, 2022

(54) METHOD FOR PEPTIDE SYNTHESIS AND APPARATUS FOR CARRYING OUT A METHOD FOR SOLID PHASE SYNTHESIS OF PEPTIDES

(71) Applicant: SULFOTOOLS GMBH, Darmstadt (DE)

(72) Inventors: Sascha Knauer, Darmstadt (DE); Tobias Michael Louis Roese, Lautertal (DE); Olga Avrutina, Darmstadt (DE); Harald Kolmar, Mühltal (DE); Christina Uth, Darmstadt (DE)

(73) Assignee: SULFOTOOLS GMBH, Darmstadt (DE)

( * ) Notice: Subject to any disclaimer, the term of this patent is extended or adjusted under 35 U.S.C. 154(b) by 0 days.

(21) Appl. No.: 15/514,833

(22) PCT Filed: Sep. 29, 2015

(86) PCT No.: PCT/EP2015/072406
§ 371 (c)(1),
(2) Date: Mar. 28, 2017

(87) PCT Pub. No.: WO2016/050764
PCT Pub. Date: Apr. 7, 2016

(65) Prior Publication Data
US 2017/0218010 A1    Aug. 3, 2017

(30) Foreign Application Priority Data

Sep. 29, 2014   (EP) .................................. EP14186879

(51) Int. Cl.
| | | |
|---|---|---|
| *C07K 1/10* | (2006.01) | |
| *C07K 1/04* | (2006.01) | |
| *C07K 1/02* | (2006.01) | |
| *C07K 1/06* | (2006.01) | |

(52) U.S. Cl.
CPC .................. *C07K 1/04* (2013.01); *C07K 1/02* (2013.01); *C07K 1/063* (2013.01); *C07K 1/064* (2013.01); *C07K 1/10* (2013.01); *Y02P 20/55* (2015.11)

(58) Field of Classification Search
None
See application file for complete search history.

(56) References Cited

U.S. PATENT DOCUMENTS 8,415,307 B1    4/2013   Curran et al.

FOREIGN PATENT DOCUMENTS

WO        013/115813        8/2013

OTHER PUBLICATIONS

Carpino, Louis A.; Han, Grace Y., 9-Fluorenylmethoxycarbonyl function, a new base-sensitive amino-protecting group Journal of the American Chemical Society (1970), 92(19), 5748-9.*
Sol 1.1 Solubility of Organic Compounds, 2017, pp. 1-3 for solubility properties of organic compounds.*
International Search Report for related PCT/EP2015/072406 dated Dec. 7, 2015.
Hubbuch, Arnulf, et al. "4-Sulfobenzyl, eine neue Carboxyschutzgruppe." Angewandte Chemie 92.5 (1980): 394-395.
Translation of Hubbuch, Arnulf, et al. "4-Sulfobenzyl, eine neue Carboxyschutzgruppe." Angewandte Chemie 92.5 (1980): 394-395.
Bindewald, Roland, et al. "4-Sulfobenzyl ester-its use in peptide synthesis." International Journal of Peptide and Protein Research 23.4 (1984): 376-383.
Bindewald, Roland, et al. "4-Sulfobenzyl ester-an anionic protecting group for peptide synthesis." International Journal of Peptide and Protein Research 23.4 (1984): 368-375. APA.
Merrifield, R. B., and Anita E. Bach. "9-(2-Sulfo) fluorenylmethyloxycarbonyl chloride, a new reagent for the purification of synthetic peptides." The Journal of Organic Chemistry 43.25 (1978): 4808-4816.
Shechter, Yoram, Haim Tsubery, and Mati Fridkin. "N-[(2-Sulfo)-9-fluorenylmethoxycarbonyl] 3-gentamicin C1 Is Long-Acting Prodrug Derivative." Journal of medicinal chemistry 45.19 (2002): 4264-4270.
Gershonov, Eytan, et al. "A novel approach for a water-soluble long-acting insulin prodrug: Design, preparation, and analysis of [(2-sulfo)-9-fluorenylmethoxycarbonyl] 3-insulin." Journal of medicinal chemistry 43.13 (2000): 2530-2537.
Cammish, Linda E., and Steven A. Kates. "Instrumentation for automated solid phase peptide synthesis." ChemInform 31.45 (2000).
Hojo, Keiko, Mitsuko Maeda, and Koichi Kawasaki. "2-(4-Sulfophenylsulfonyl) ethoxycarbonyl group: a new water-soluble N-protecting group and its application to solid phase peptide synthesis in water." Tetrahedron letters 45.50 (2004): 9293-9295.
Amblard, Muriel et al. "Methods and Protocols of Modem Solid Phase Peptide Synthesis", Molecular Biotechnology, 2006, pp. 239-254, vol. 33.
Erickson, Bruce W., et al. "Solid-phase peptide synthesis." The proteins (1976): 255-527.
Hojo, Keiko, et al., "A new water-soluble N-protecting group, 2-[phenyl (methyl) sulfonio] ethyloxycarbonyl tetrafluoroborate, and its application to solid phase peptide synthesis in water." Journal of Peptide Science: An Official Publication of the European Peptide Society, 2001, pp. 615-618, vol. 7., No. 12.

(Continued)

*Primary Examiner* — Thomas S Heard
(74) *Attorney, Agent, or Firm* — Barnes & Thornburg LLP; Ryan L. Marshall

(57) ABSTRACT

The invention relates to a method for peptide synthesis, wherein said method comprises the steps of reacting a first amino acid or a first peptide with an α-amine protected second amino acid in a solvent selected from the group consisting of water, alcohol, and a mixture of water and alcohol, and removing the α-amine protecting group with a deprotecting solution. The invention further relates to protective agents, their use and an apparatus for carrying out a method for solid phase synthesis of peptides.

13 Claims, 1 Drawing Sheet

(56) References Cited

OTHER PUBLICATIONS

Hojo, Keiko, et al. "Development of a method for environmentally friendly chemical peptide synthesis in water using water-dispersible amino acid nanoparticles." Chemistry Central Journal, 2011, pp. 1-10, vol. 5, No. 1.

Santini, Richard, et al., "A measure of solvent effects on swelling of resins for solid phase organic synthesis." Tetrahedron Letters, 1998, pp. 8951-8954, vol. 39, No. 49.

\* cited by examiner

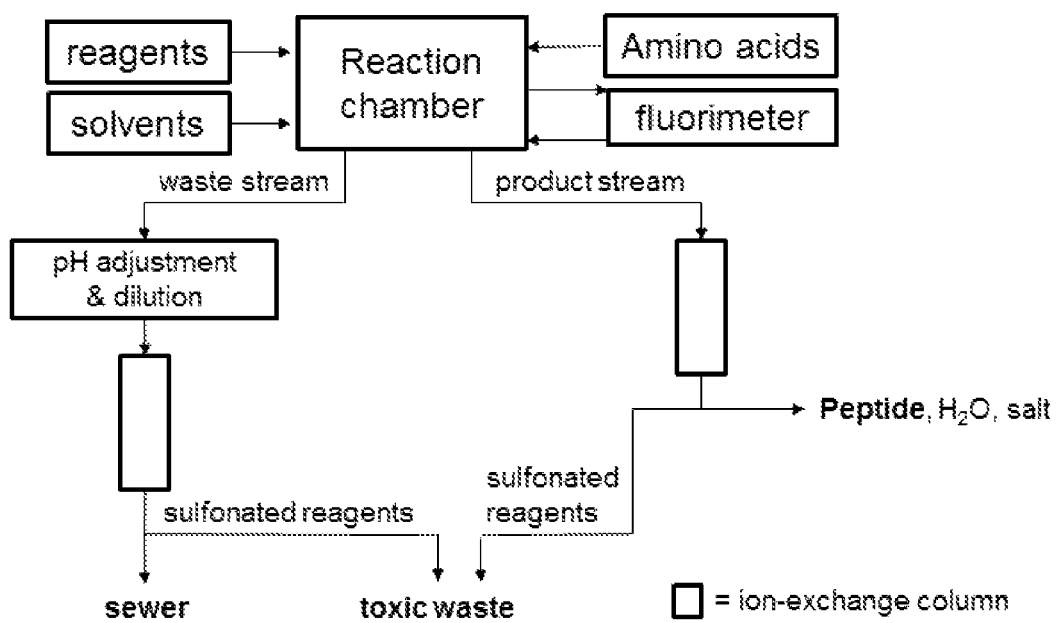

METHOD FOR PEPTIDE SYNTHESIS AND APPARATUS FOR CARRYING OUT A METHOD FOR SOLID PHASE SYNTHESIS OF PEPTIDES

The present invention relates to a method for peptide synthesis in a solvent selected from the group consisting of water, alcohol, and a mixture of water and alcohol, to compounds used in this method, and to an apparatus for carrying out a method for solid phase synthesis of peptides.

BACKGROUND OF THE INVENTION

Peptides are linked chains of amino acids and represent the precursors of proteins. Peptides and proteins are the elementary components of all living systems and are involved in a variety of processes of life. They have many applications in medicine and biological sciences. As a consequence, the capability to synthesize peptides and proteins is of high significance to human life.

Hence, the synthetic production of peptides is of significant interest. Peptides are synthesized by coupling the carboxyl group (C-terminus) of one amino acid to the amino group or N-terminus of another. Solid-phase peptide synthesis (SPPS) was introduced by Merrifield et al. in 1963 with the intent to overcome the intermediate purification problems associated with peptide assembly in solution (see Stewart and Young, Solid Phase Peptide Synthesis (*Pierce Chemical Co.*, 2d ed., 1984), Chan and White, Fmoc Solid Phase Peptide Synthesis: A Practical Approach (Oxford University Press, 2000)). Upon solid-phase synthesis, amino acids are consecutively coupled to result in a peptide possessing the desired sequence while the C-terminus is anchored to an insoluble polymeric support (solid phase). Once the desired sequence has been assembled, the peptide is cleaved from the solid support.

This synthetic schema requires the protection of the α-amino group of the incoming amino acid in order to avoid self-polymerization. The standard protecting groups for α-amino functions are the acid-labile tert-butyloxycarbonyl (Boc) group, the base-labile fluorenylmethyloxycarbonyl (Fmoc) group and the allyloxycarbonyl (Alloc) group which is removed under neutral conditions of Pd catalysis in the presence of PhSiH$_3$ as scavenger for the allyl system.

Methods for solid-phase peptide synthesis following any of the three above-mentioned α-amino protection schemes generally require additional protection of reactive side chains of the constituent amino acids from unwanted chemical transformations. Therefore, it is necessary that these protecting groups are resistant to the agents used during the coupling cycle. Additionally, the linkage of the growing peptide to the solid-phase support has to be stable towards the conditions of the α-amino deprotection and chain assembly.

In the case of the Fmoc-based α-amino protection, the side-chain groups should be resistant to the basic reagents used to remove the Fmoc moiety. The side-chain protecting groups are generally removed by mild acidic reagents after the peptide chain has been assembled. These side chain protecting groups are generally cleaved by anhydrous HF, trifluoromethanesulfonic acid or trifluoro acetic acid (TFA) after the desired peptide chain has been assembled.

The peptide assembly procedure is typically performed in polar aprotic organic solvents such as dimethyl formamide (DMF), N-methylpyrrolidone (NMP), dimethyl sulfoxide (DMSO) and dichloromethane (DCM), or a mixture of these organic solvents because of the strong hydrophobic character of the α-amino protecting groups Fmoc and Boc, which are insoluble in water and which are frequently used in SPPS. Additionally, the side-chain protecting groups commonly used in SPPS are usually hydrophobic and render the amino acid insoluble in water.

SPPS approaches applying Fmoc and Boc protection are widely used but suffer from the need for the previously mentioned organic solvents which are costly and toxic. DMF, for example, comes with considerable health and environmental risks; it has been linked to cancer in humans, and it is suspected to cause birth defects. Hence, the use of these toxic solvents requires special technical equipment and precautions, as e.g. performing the reaction under the fume hood and handling by highly specialized personnel. In addition, the disposal of the used solvent is problematic and expensive. As a consequence, SPPS using organic solvents is expensive and restricted to specialised laboratories with special equipment for organic chemistry synthesis.

Therefore, a water based scheme for peptide synthesis and in particular SPPS, is highly desirable in order to avoid the previously mentioned problems.

As an attempt to overcome this problem, Hojo et al. proposed the use of water-soluble protecting groups (*Chem. Pharm. Bull.* 2004, 52, 422-427 and *Tetrahedron Lett.* 2004, 45, 9293.) They developed several protecting groups for this purpose, among them 2-(Phenyl(methyl)sulfonyl)ethyloxycarbonyl tetrathioborate (Pms), Ethanesulfonylethoxycarbonyl (Esc), and 2-(4-Sulfophenylsulfonyl)ethoxy carbonyl (Sps). In WO 2013 115813 A1 CEM Corporation claims the deprotection of α,β-unsaturated sulfones in water or aqueous systems and their usage in water-based SPPS.

However, the above mentioned protecting groups have several major disadvantages, which are their restricted stability (e.g. for Pms), their moderate solubility (Esc), and their expensive and complicated synthesis and restricted usability, which e.g. excludes cysteine and methionine since autooxidation of their sulfur groups occurs (Sps). As a secondary consideration, these α-amine protecting groups do not show selective absorption, UV or fluorescence signals that can be used to detect the amount of coupled amino acid or for providing an indication of the extent to which deprotection has proceeded. Unlike the conventional Fmoc group, Pms and Esc cannot be tracked in conventional UV monitoring. Sps can he monitored by UV, but the difficult and costly synthesis of Sps tends to discourage its usage. As a result, the increased water solubility of these compounds is not a sufficient solution to the problems of water based SPPS in an overall sense.

Therefore, it is an object of the invention to provide an improved method and apparatus for water compatible reaction systems for peptide synthesis in general and solid phase peptide synthesis in particular.

DESCRIPTION OF THE INVENTION

In an embodiment the present invention relates to a protective agent suitable for forming protecting groups on functional groups on a peptide and/or amino acid during water based peptide synthesis, wherein the functional group to be protected is preferably selected from amine, alcohol, thiol and carboxyl groups, wherein the protective agent comprises I. a backbone structure,
II. at least one water-solubility enhancing functional group and
III. at least one reactive group,
   wherein the backbone structure comprises a moiety selected from the group consisting of 9-methylfluorene, t-butane and/or mono-, di or triphenylmethane, preferably the backbone structure consists of such a moiety,
   wherein the water-solubility enhancing functional group is selected from the group consisting of $SO_3^-$, $PO_3^{2-}$, $N(CH_3)_2$, $N(CH_3)_3^+$, CN, $OSO_3^-$ ester, $OPO_3^{2-}$ ester and combinations thereof, and
   wherein the water-solubility enhancing functional group and the reactive group are attached to the backbone structure via at least one covalent bond.

This invention also relates to the use of said compounds for protecting a functional group in a chemical reaction. In preferred embodiments the agents are used for forming protecting groups on functional groups on a peptide and/or amino acid during water based peptide synthesis. Preferably, the functional group to be protected is preferably selected from amine, alcohol, thiol and carboxyl groups.

In preferred embodiments the water-solubility enhancing functional group is selected from the charged functional groups $SO_3^-$, $PO_3^{2-}$, $OSO_3^-$ ester, $OPO_3^{2-}$ ester and $N(CH_3)_3^+$. Using charged functional groups as the water solubility enhancing functional group has proven useful for increasing water solubility more efficiently than the uncharged functional groups. The protective agent may comprise one or more water-solubility enhancing functional groups, in preferred embodiments the protective agent comprises more than one water-solubility enhancing functional group. In further preferred embodiments the protective agent comprises at least two water-solubility enhancing functional groups. In other preferred embodiments the protective agent comprises from 1 to 8, 2 to 7, or 3 to 4 water-solubility enhancing functional groups. The inventors have found out that it may be useful to have more than one water solubility enhancing functional group in the protective agent molecule because the water solubility is increased to a greater extent. In embodiments where the backbone structure is t-butane or phenylmethane one water solubility enhancing functional group may be sufficient.

In preferred embodiments of this invention, the protective agent comprises water solubility enhancing functional groups that are all of the same kind, in particular, all of the kind $SO_3^-$. In alternative embodiments, the protective agent comprises water solubility enhancing functional groups of different kinds. In as far as the water solubility enhancing functional group is $SO_3^-$, it is preferred that the protective agent comprises at least 2 of these functional groups. Synthesis of the protective agent can be more efficient and easier, if the water solubility enhancing functional groups are all of the same kind.

The backbone structure comprises a moiety selected from the group consisting of 9-methylfluorene, t-butane and/or mono-, di- or triphenylmethane. In preferred embodiments, the backbone structure is selected from 9-methylfluorene and t-butane.

The reactive group is suitable, i.e. has the required chemical reactivity, to undergo a chemical reaction with the functional group to be protected. It is preferably selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups. When the backbone structure is 9-methylfluorene the reactive group is preferably selected from oxycarbonyl halogenide, oxycarbonyl Oxyma ester and oxycarbonyl O-succinimide. When the backbone structure is t-butane the reactive group is preferably selected from hydroxide, halogenide, thiol, oxycarbonyl O-succinimide and oxycarbonyl anhydride. When the backbone structure is selected from mono-, di- and triphenylmethane the reactive group is preferably selected from halogenide, oxymethyl halogenide and oxycarbonyl halogenide.

Preferred protective agents having the 9-methylfluorene backbone structure of the present invention can be illustrated by the following general formula 1:

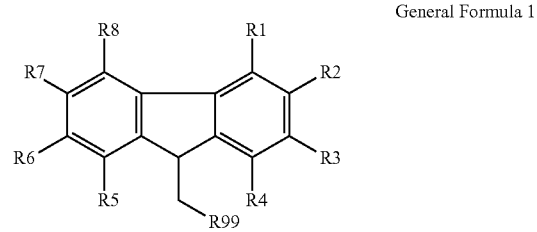

General Formula 1 wherein R1 to R8 are independently selected from hydrogen, $SO_3^-$, $PO_3^{2-}$, $N(CH_3)_2$, $N(CH_3)_3^+$, $OSO_3^-$ ester, $OPO_3^{2-}$ ester and CN with the proviso that at least one, preferably at least two of R1 to R8 is selected from $SO_3^-$, $PO_3^{2-}$, $N(CH_3)_2$, $N(CH_3)_3^+$, $OSO_3^-$ ester, $OPO_3^{2-}$ ester and CN. In preferred embodiments all of R1 to R8 that are not $SO_3^-$, $PO_3^{2-}$, $N(CH_3)_2$, $N(CH_3)_3^+$, $OSO_3^-$ ester, $OPO_3^{2-}$ ester or CN are hydrogen.

R99 is preferably selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups, wherein R99 is preferably selected from oxycarbonyl halogenide, oxycarbonyl Oxyma ester and oxycarbonyl O-succinimide.

In preferred embodiments R2 and R7 are selected from $SO_3^-$, $PO_3^{2-}$, $N(CH_3)_2$, $N(CH_3)_3^+$, $OSO_3^-$ ester, $OPO_3^{2-}$ ester and CN, in particular R2 and R7 are $SO_3^-$. Preferably, R1, R3 to R6 and R8 are hydrogen.

In preferred embodiments R3 and R6 are selected from $SO_3^-$, $PO_3^{2-}$, $N(CH_3)_2$, $N(CH_3)_3^+$, $OSO_3^-$ ester, $OPO_3^{2-}$ ester and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $N(CH_3)_2$, $N(CH_3)_3^+$, $OSO_3^-$ ester, $OPO_3^{2-}$ ester and CN, in particular R2 and R6 are $SO_3^-$. Preferably, R1, R3, R4, R5, R7 and R8 are hydrogen.

Preferred protective agents having the 9-methylfluorene backbone structure of the present invention are shown in the following table 1. The compounds listed in the table are in no way limiting the scope of the present invention. They constitute illustrative and preferable protective agents according to this invention.

TABLE 1
| # | Protective agent | backbone | H₂O solubility enhancing group | reactive group | protected group |
|---|---|---|---|---|---|
| 1 | 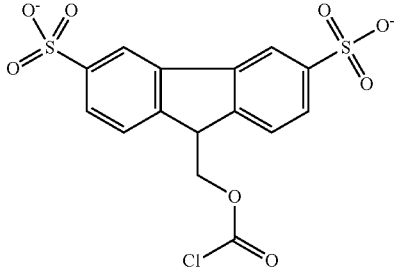 [SMILES: O=C(Cl)OCC1c2ccc(S(=O)(=O)[O-])cc2-c2cc(S(=O)(=O)[O-])ccc21] | 9-methyl-fluorene | 2x $SO_3^-$ | oxycarbonyl halogenide | amine |
| 2 | 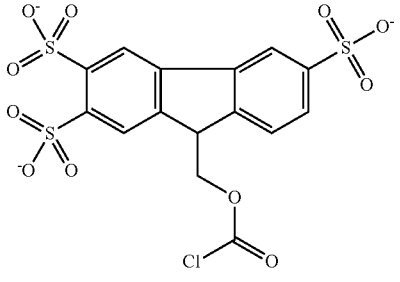 | 9-methyl-fluorene | 3x $SO_3^-$ | oxycarbonyl halogenide | amine |
| 3 | 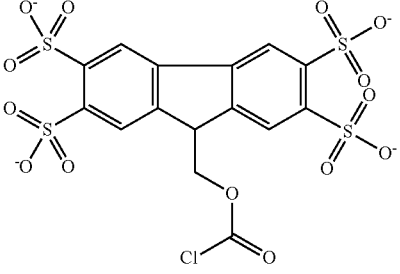 | 9-methyl-fluorene | 4x $SO_3^-$ | oxycarbonyl halogenide | amine |
| 4 | 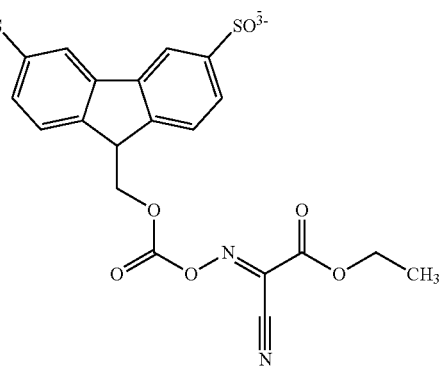 | 9-methyl-fluorene | 2x $SO_3^-$ | Oxyma ester | amine |

TABLE 1-continued

| # | Protective agent | backbone | H₂O solubility enhancing group | reactive group | protected group |
|---|---|---|---|---|---|
| 5 | (structure) | 9-methyl-fluorene | 2x SO₃⁻ | Oxyma B ester | amine |
| 6 | (structure) | 9-methyl-fluorene | 2x SO₃⁻ | oxycarbonyl O-succinimide | amine |
| 7 | (structure) | 9-methyl-fluorene | 2x SO₃⁻ | oxycarbonyl halogenide | amine |
| 8 | (structure) | 9-methyl-fluorene | 2x N(CH₃)₂ | oxycarbonyl halogenide | amine |
| 9 | (structure) | 9-methyl-fluorene | 2x N(CH₃)₃⁺ | oxycarbonyl halogenide | amine |

TABLE 1-continued

| # | Protective agent | backbone | H₂O solubility enhancing group | reactive group | protected group |
|---|---|---|---|---|---|
| 10 | | 9-methyl-fluorene | $N(CH_3)_3{}^+CN$ | oxycarbonyl halogenide | amine |

Preferred protective agents having the t-butane backbone structure of the present invention can be illustrated by the following general formula 2:

limiting the scope of the present invention. They constitute illustrative and preferable protective agents according to this invention.

TABLE 2

| # | Protective agent | backbone | H2O solubility enhancing group | reactive group | protected group |
|---|---|---|---|---|---|
| 11 | | t-butane | $SO_3{}^-$ | hydroxide | carboxyl |
| 12 | | t-butane | $SO_3{}^-$ | thiol | thiol |
| 13 | | t-butane | $SO_3{}^-$ | bromide | alcohol |
| 14 | | t-butane | $SO_3{}^-$ | oxycarbonyl O-succinimide | amine |

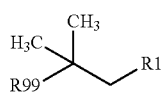

General Formula 2 wherein R1 is selected from $SO_3{}^-$, $PO_3{}^{2-}$, $N(CH_3)_2$, $N(CH_3)_3{}^+$, $OSO_3{}^-$ ester, $OPO_3{}^{2-}$ ester and CN. In preferred embodiments R1 is $SO_3{}^-$. R99 is preferably selected from the group consisting of oxycarbonyl halogenide, oxycarbonyl O-succinimide, oxycarbonyl anhydride, halogenide, oxymethyl halogenide, hydroxide and thiol groups, wherein R99 is more preferably selected from hydroxide, halogenide, thiol, oxycarbonyl O-succinimide and oxycarbonyl anhydride.

Preferred protective agents having the t-butane backbone structure of the present invention are shown in the following table 2. The compounds listed in the table are in no way Preferred protective agents having the mono-, di or triphenylmethane backbone structure of the present invention can be illustrated by the following general formula 3, 4 or 5, respectively:

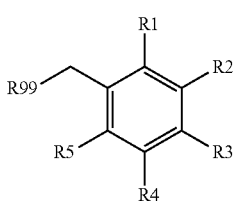

General Formula 3 wherein R1 to R5 are independently selected from hydrogen, $SO_3{}^-$, $PO_3{}^{2-}$, $N(CH_3)_2$, $N(CH_3)_3{}^+$, $OSO_3{}^-$ ester, $OPO_3{}^{2-}$ ester and CN with the proviso that at least one, preferably at least two of R1 to R5 are selected from $SO_3{}^-$, $PO_3^{2-}$, $N(CH_3)_2$, $N(CH_3)_3^+$, $OSO_3^-$ ester, $OPO_3^{2-}$ ester and CN. In preferred embodiments all of R1 to R5 that are not $SO_3^-$, $PO_3^{2-}$, $N(CH_3)_2$, $N(CH_3)_3^+$, $OSO_3^-$ ester, $OPO_3^{2-}$ ester or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide.

In preferred embodiments R3 is selected from $SO_3^-$, $PO_3^{2-}$, $N(CH_3)_2$, $N(CH_3)_3^+$, $OSO_3^-$ ester, $OPO_3^{2-}$ ester and CN, in particular R3 is $SO_3^-$. Preferably, R1, R2, R4 and R5 are hydrogen.

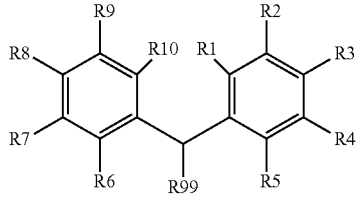

General Formula 4 wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R10 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

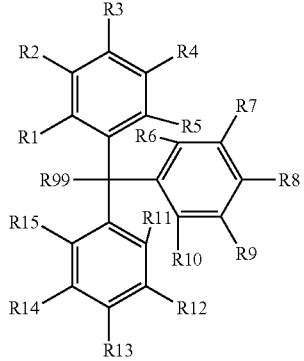

General Formula 5 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

R99 is preferably selected from the group consisting of oxycarbonyl halogenide, oxycarbonyl Oxyma ester, oxycarbonyl O-succinimide, oxycarbonyl anhydride, halogenide, oxymethyl halogenide, hydroxide and thiol groups, wherein R99 is more preferably selected from halogenide, oxymethyl halogenide and oxycarbonyl halogenide. In a particularly preferred embodiment R99 is not halogenide, when R3, R8 and R13 are $SO_3^-$. In another particularly preferred embodiment R99 is not chloride, when R3, R8 and R13 are $SO_3^-$. In a preferred embodiment R99 is preferably selected from the group consisting of oxycarbonyl halogenide, oxycarbonyl Oxyma ester, oxycarbonyl O-succinimide, oxycarbonyl anhydride, oxymethyl halogenide, hydroxide and thiol groups. In particularly preferred embodiment R99 is not halogenide, particularly not chloride.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

Preferred protective agents having the mono-, di or triphenylmethane backbone structure of the present invention are shown in the following table 3. The compounds listed in the table are in no way limiting the scope of the present invention. They constitute illustrative and preferable protective agents according to this invention.

TABLE 3

| # | Protective agent | backbone | H2O solubility enhancing group | reactive group | protected group |
|---|---|---|---|---|---|
| 15 | ![structure] | phenyl-methane | $SO_3^-$ | oxycarbonyl-halogenide | amine |

TABLE 3-continued

| # | Protective agent | backbone | H2O solubility enhancing group | reactive group | protected group |
|---|---|---|---|---|---|
| 16 | | phenyl-methane | $SO_3^-$ | halogenide | alcohol |
| 17 | | phenyl-methane | $SO_3^-$ | oxymethyl-halogenide | alcohol |
| 18 | | diphenyl-methane | 2x $SO_3^-$ | oxycarbonyl-halogenide | amine |
| 19 | | triphenyl-methane | 3x $SO_3^-$ | halogenide | alcohol |

This invention also relates to the use of the protective agents for protecting a functional group in a chemical reaction. Preferably, the functional group is present on an amino acid, peptide or protein and the chemical reaction is peptide or protein synthesis in a solvent selected form water, alcohol or a mixture of water and alcohol.

Method

The invention relates to a method for peptide synthesis comprising the steps of reacting a first amino acid or a first peptide with an α-amine protected second amino acid or second peptide in a solvent selected from the group consisting of water, alcohol, and a mixture of water and alcohol, and removing the α-amine protecting group with a deprotecting solution, characterized in that the α-amine protecting group is the reaction product of one of the protective agents described herein with an α-amine functional group of the second amino acid or second peptide. In preferred embodiments, the α-amine protecting group is at least one of the following formulas 6 to 10. In each case the nitrogen shown in the following general formula belongs to the protected amino group:

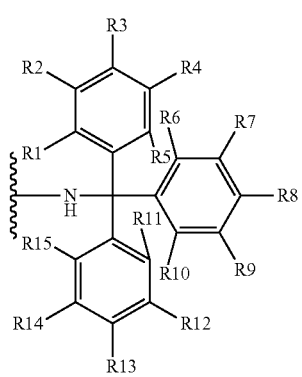

General Formula 6 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $N(CH_3)_2$, $OSO_3^-$ ester, $OPO_3^{2-}$ ester, $N(CH_3)_3^+$ and CN. In preferred embodiments all of R1 to R15 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

In preferred embodiments R3, R8 and R13 are selected from $SO_3^-$, $PO_3^{2-}$, $OSO_3^-$ ester, $OPO_3^{2-}$ ester, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

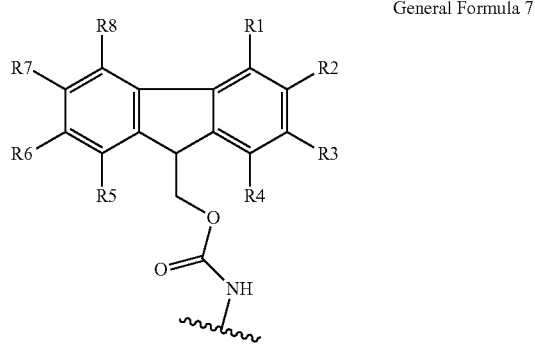

General Formula 7 wherein R1 to R8 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R8 is selected from $SO_3^-$, $OSO_3^-$ ester, $OPO_3^{2-}$ ester, $PO_3^-$, $N(CH_3)_2$, $N(CH_3)_3^+$ and CN. In preferred embodiments all of R1 to R8 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R2 and R7 are selected from $SO_3^-$, $OSO_3^-$ ester, $OPO_3^{2-}$ ester, $PO_3^{2-}$, $N(CH_3)_2$, $N(CH_3)_3^+$ and CN, in particular R2 and R7 are $SO_3^-$. Preferably, R1, R3 to R6 and R8 are hydrogen.

In preferred embodiments R3 and R6 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $OSO_3^-$ ester, $OPO_3^{2-}$ ester, $N(CH_3)_2$, $N(CH_3)_3^+$ and CN, in particular R2 and R6 are $SO_3^-$. Preferably, R1, R3, R4, R5, R7 and R8 are hydrogen.

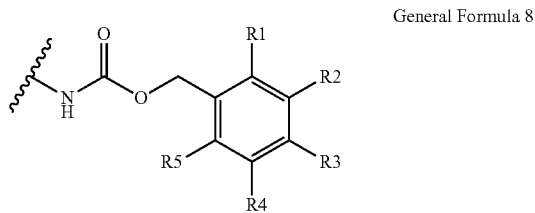

General Formula 8 wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R5 that are not $SO_3^-$, $PO_3^{2-}$, $N(CH_3)_2$, $OSO_3^-$ ester, $OPO_3^{2-}$ ester, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

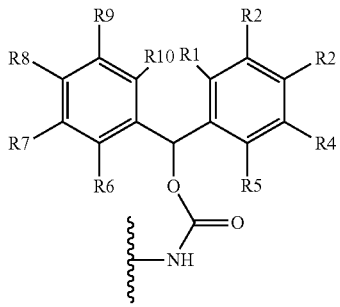

General Formula 9 wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R10 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

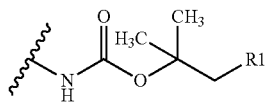

General Formula 10 wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

In particularly preferred embodiments the α-amine protecting group is a 9-(3,6-disulfo)fluorenylmethyloxy-carbonyl group, 9-(2,7-disulfo)fluorenylmethyloxy-carbonyl group or a tert-butyl-(2-sulfonate)oxycarbonyl group (Sboc). As used herein, the term "Smoc" denotes a 9-(3,6-disulfo)fluorenylmethyloxy-carbonyl group or a 9-(2,7-disulfo)fluorenylmethyloxy-carbonyl group.

The structure of the protected amino acids and peptides according to this invention, in particular Smoc and Sboc protected amino acids, is more soluble in water as compared to protected amino acids or peptides in the prior art, in particular Fmoc and Boc protected amino acids. The reason is that in the present invention water solubility enhancing functional groups are added to the protecting agents, in particular sulfo ($SO_3$) groups. Therefore, one of the advantages of the invention is the utilization of an amino acid and/or peptide that is soluble in water in its protected form, and the capability to use only water, only alcohol, or only a water-alcohol mixture for peptide synthesis, i.e. without other solubility-enhancing additives and without the need to use toxic solvents. Performing peptide synthesis in a non-toxic water and/or alcohol containing solvent offers various advantages for use in pharmaceutical and biological applications.

Preferred solvents are water and water-alcohol mixtures with water being the most preferred solvent. Preferred alcohols are methanol, ethanol, isopropanol, 2-propanol, n-propanol, n-butanol, isobutanol, sec-butanol, tert-butanol, or a mixture thereof.

As used herein, the term "soluble in water in its protected form" means that the composition has the degree of solubility necessary for the desired reaction to proceed in an aqueous solvent system. As in the case with any composition, the term "soluble" does not imply unlimited solubility in any or all amounts.

The deprotecting solutions that are suitable for use in the present invention preferably comprise an acid or base, preferably an aqueous acid or base, i.e. the acid and/or base preferably is water-soluble. Preferred acids are phosphoric acid, hydrochloric acid or trifluoro acetic acid. Preferred bases are amines and ammonia. Preferred deprotecting solutions are amine and/or ammonia solutions. The base is used in an amount and to the extent necessary to deprotect the functional group. The solubility of certain organic bases may limit the amount that can be dissolved in the water, alcohol or mixture of water and alcohol. Suitable bases are those having a solubility that allows for dissolving a sufficient amount to carry out the deprotection in the selected solvent.

The deprotecting solution for deprotecting a Sboc group preferably comprises an aqueous acid, such as phosphoric acid, hydrochloric acid or trifluoro acetic acid.

The deprotecting solution for deprotecting a Smoc group preferably comprises a water soluble base such as amine or ammonia. The water soluble base is used in an amount and to the extent necessary to deprotect the peptide. The solubility of certain organic bases may limit the amount that can be dissolved in the water, alcohol or mixture of water and alcohol. Suitable bases are those having a solubility that allows for dissolving a sufficient amount to carry out the deprotection in the selected solvent.

It will be understood that after deprotection, the reaction and deprotection steps can be repeated using further amino acids or further peptides wherein the α-amino group of said further amino acid and/or further peptide is preferably protected with a protecting group according to this invention, in particular an Smoc group or an Sboc group, until the desired target peptide is obtained.

In a preferred embodiment of the invention, any reactive side chain functional group of said first amino acid or first peptide and/or said second amino acid or second peptide is protected with a side chain protecting group, which preferably comprises at least one water solubility enhancing functional group. The side chain protecting group may comprise a sulfonic group or a sulfonic ester. The method preferably comprises the step of removing the side chain protecting groups. The water solubility enhancing functional group of the side chain protecting group provides water solubility to the side chain protected amino acid or peptide. Suitable side chain protecting groups are the reaction products of one of the protective agents mentioned above with the respective side chain functional group of the amino acid or peptide.

Regarding the side chain protecting groups, preferred amine protecting groups are those shown in the following formulae 11 to 15, wherein the nitrogen belongs to the protected amino group.

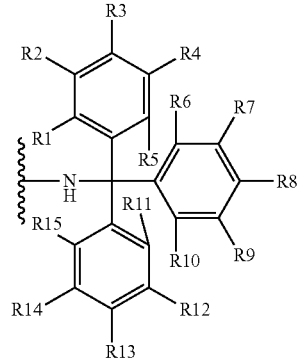

General Formula 11 wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

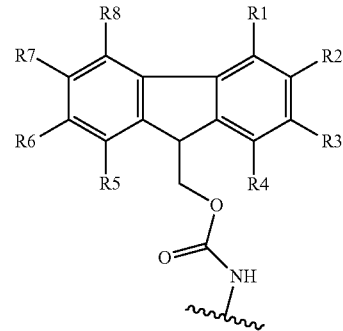

General Formula 12 wherein R1 to R8 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R8 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R8 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R2 and R7 are selected from $SO_3^-$, $OSO_3^-$ ester, $OPO_3^{2-}$ ester, $PO_3^{2-}$, $N(CH_3)_2$, $N(CH_3)_3^+$ and CN, in particular R2 and R7 are $SO_3^-$. Preferably, R1, R3 to R6 and R8 are hydrogen.

In preferred embodiments R3 and R6 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R6 are $SO_3^-$. Preferably, R1, R2, R4, R5, R7 and R8 are hydrogen.

In preferred embodiments R2 and R6 are selected from $SO_3^-$, $PO_3^{2-}$, $OSO_3^-$ ester, $OPO_3^{2-}$ ester, $N(CH_3)_2$, $N(CH_3)_3^+$ and CN, in particular R2 and R6 are $SO_3^-$. Preferably, R1, R3, R4, R5, R7 and R8 are hydrogen.

General Formula 13

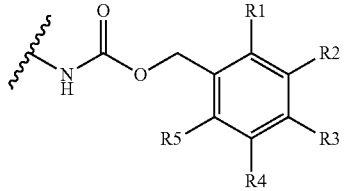

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

General Formula 14

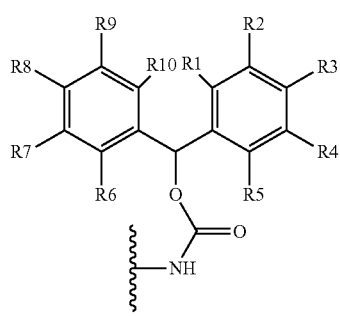

wherein R1 to R10 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R10 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R10 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 and R8 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3 and R8 are selected from $SO_3^-$. Preferably, R1, R2, R4 to R7, R9 and R10 are hydrogen.

General Formula 15

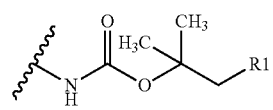

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

In particularly preferred embodiments, the side chain amine protecting group is selected from 9-(3,6-disulfo) fluorenylmethyloxy-carbonyl group, 9-(2,7-disulfo)fluorenylmethyloxy-carbonyl group, tri(4-sulfophenyl)methyl group (SulfoTrt), tert-butyl-(2-sulfonate)oxycarbonyl group (Sboc) and 4-sulfo-carbobenzyloxy group (SulfoCBz).

Preferred alcohol protecting groups are shown in the following formulae 16 to 19:

General Formula 16

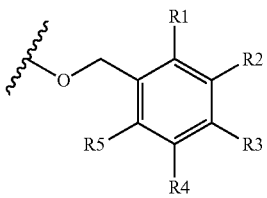

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

General Formula 17

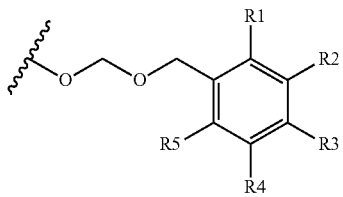

wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $PO_3^{2-}$, $OSO_3^-$ ester, $OPO_3^{2-}$ ester, $N(CH_3)_2$, $N(CH_3)_3^+$ and CN, in particular R3 is $SO_3^-$. Preferably, R1, R2, R4 and R5 are hydrogen.

General Formula 18

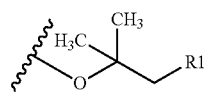

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

General Formula 19

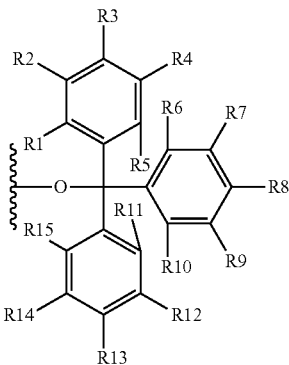

wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $PO_3^{2-}$, $OSO_3^-$ ester, $OPO_3^{2-}$ ester, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

In particularly preferred embodiments the alcohol protecting groups are selected from 4-sulfobenzyl group (BzS), 4-sulfo-benzyloxymethyl group (BOMS), tri(4-sulfophenyl)methyl group (SulfoTrt) and tert-butyl-1-sulfonate group (tBuS).

Preferred thiol protecting groups are shown in the following formulae 20 and 21:

General Formula 20

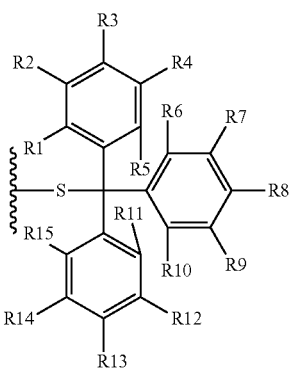

wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

General Formula 21

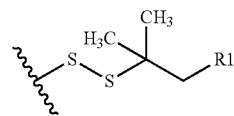

wherein R1 is selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments R1 is $SO_3^-$.

In particularly preferred embodiments the thiol protecting group is selected from tri(4-sulfophenyl)methyl group (SulfoTrt) and 1-sulfo-2-methyl-2-propanethiol group (St-BuS).

Preferred carboxyl protecting groups are those shown in the following formulae 22 to 25:

General Formula 22

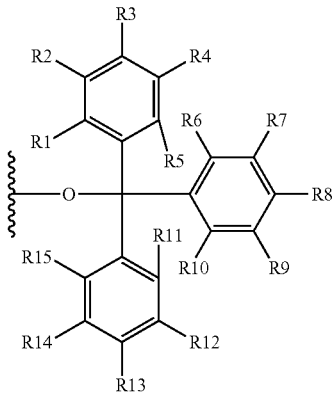

wherein R1 to R15 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two, most preferably at least three of R1 to R15 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R15 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3, R8 and R13 are selected from $SO_3^-$, $OSO_3^-$ ester, $OPO_3^{2-}$ ester, $PO_3^{2-}$, $N(CH_3)_2$, $N(CH_3)_3^+$ and CN, in particular R3, R8 and R13 are $SO_3^-$. Preferably, R1, R2, R4 to R7, R9 to R12, R14 and R15 are hydrogen.

General Formula 23

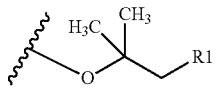

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments R1 is $SO_3^-$.

General Formula 24

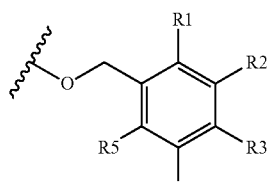

Amine protecting groups

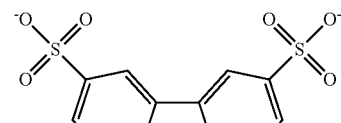

Smoc wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

General Formula 25

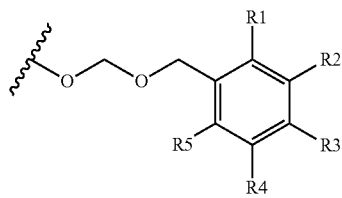

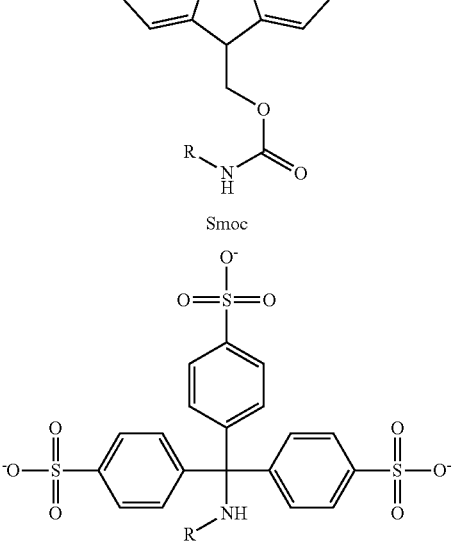

Sulfo-Trt

Sboc

SulfoCbz

Alcohol protecting groups

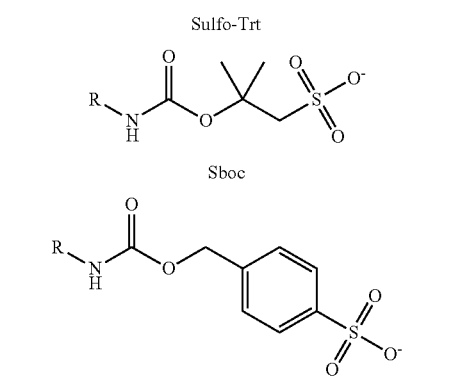

BzS wherein R1 to R5 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R5 are selected from $SO_3^-$, $PO_3^{2-}$, $OSO_3^-$ ester, $OPO_3^{2-}$ ester, $N(CH_3)_2$, $N(CH_3)_3^+$ and CN. In preferred embodiments all of R1 to R5 that are not $SO_3^-$, $OSO_3^-$ ester, $OPO_3^{2-}$ ester, $PO_3^{2-}$, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

In particularly preferred embodiments the carboxyl protecting groups are selected from 4-sulfobenzyl group (BzS), 4-sulfo-benzyloxymethyl group (BOMS), tri(4-sulfophenyl) methyl (SulfoTrt) group and tert-butyl-1-sulfonate group (tBuS).

The following is an overview over the most preferred protecting groups.

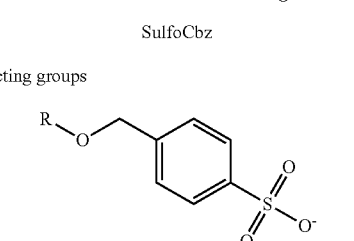

BOMS

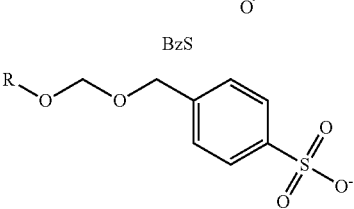

tBus

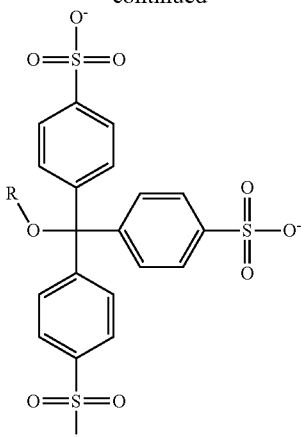

Sulfo-Trt

Thiol protecting groups

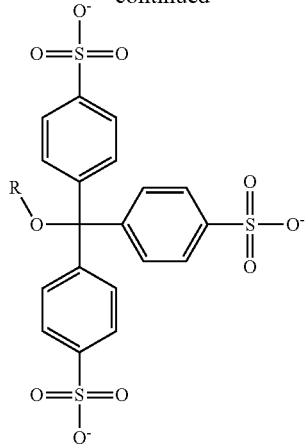

Sulfo-Trt

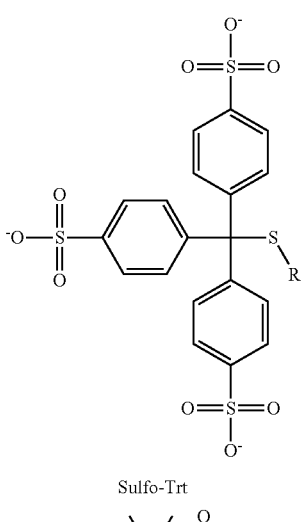

Sulfo-Trt

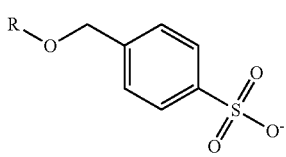

StBuS

Carboxyl protecting groups

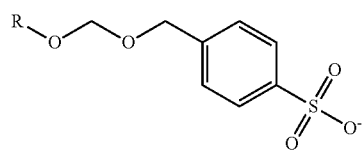

BzS

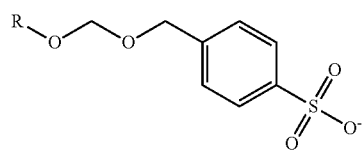

BOMS

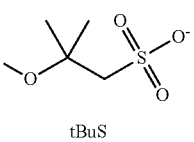

tBuS

In a further preferred embodiment of the invention, the method is an improvement of solid phase peptide synthesis, wherein the C-terminus of said first amino acid or first peptide is anchored to an insoluble support, which preferably is polymeric. By using an insoluble support, intermediate purification effort of the growing peptide is minimized. Purification can be easily performed by washing the anchored peptide after each reaction step in a solvent preferably selected from the group consisting of water, alcohol, and mixtures of water and alcohol.

In an embodiment, the method further comprises the step of cleaving the resulting peptide from the polymeric support with a cleaving composition when the peptide is complete.

Suitable cleaving compositions and methods are well known to a skilled person. Typically, an acid, such as trifluoroacetic acid and hydrofluoric acid (HF), is used to carry out the cleaving step. Preferably, an acid suitable for cleaving the desired peptide from the polymeric support concurrently removes side chain protecting groups that are attached to the amino acids in the target peptide.

Preferably, cleavage is carried out in the presence of scavenger compositions (e.g. water, phenol, DTT, triethylsilane and anisole), which protect the peptide from undesired side reactions during and after the cleaving step. A skilled person can select a suitable scavenger with regard to the protecting groups that are present.

The cleaved peptide can be separated from the cleaved support (e.g. a resin) by filtration and the peptide can then be recovered from the filtrate by a conventional step such as evaporation or solvent-driven precipitation.

In a particularly preferred embodiment of the invention, the α-amine protecting group comprises a fluorescent structure, particularly a 9-methylfluorene backbone structure and the method further comprises the step of monitoring the degree of formation of peptide bonds and/or monitoring the degree of removal of the α-amine protecting group by measuring fluorescence that is generated by the α-amine protecting groups coupled to the first amino acid or first peptide. In preferable embodiments the protecting group comprising the 9-methylfluorene backbone structure is a 9-(3,6-disulfo)fluorenylmethyloxy-carbonyl group or a 9-(2,7-disulfo)fluorenylmethyloxy-carbonyl group.

In solid phase peptide synthesis, the monitoring of the degree of formation of peptide bonds and/or monitoring the degree of removal of the fluorescent protecting group (e.g. Smoc) is achieved by monitoring the changes in fluorescence intensity after illuminating the support with UV light and measuring fluorescence that is generated by the fluorescent protecting groups coupled to the insoluble support material via the first amino acid or first peptide.

It was surprisingly observed that the 9-methylfluorene containing protecting groups, e.g. the 9-(3,6-disulfo)fluorenylmethyloxy-carbonyl group and the 9-(2,7-disulfo)fluorenylmethyloxy-carbonyl group, have intrinsic fluorescent properties. The fluorescent property of these protecting groups presents opportunities for monitoring after completion of either or both of the deprotection and coupling reactions. In some preferred embodiments of this invention, the protecting agents and the respective protecting groups contain two or more sulfo groups attached to an aromatic fluorenyl ring system, e.g. the 9-(3,6-disulfo)fluorenylmethyloxy-carbonyl group and the 9-(2,7-disulfo)fluorenylmethyloxy-carbonyl group. The two or more sulfo ($SO_3^-$) groups attached to the aromatic fluorenyl ring system in these compounds are unique compared to common reagents used during the stepwise assembly of the peptide during SPPS. These compounds, such as Smoc, can be monitored by their intrinsic fluorescence in order to determine the quantitative amounts of compound present at the end of each reaction step.

Evidence of the fluorescent (e.g. Smoc) group on the support can be used to determine successful coupling of the fluorescently protected amino acid in order to decide whether or not the coupling step has to be repeated for substantially completing the formation of peptide bonds. Likewise, evidence of the fluorescent group on the support can be used to determine an incomplete removal of the fluorescent group at the end of the deprotection step in order to decide whether or not the deprotecting step has to be repeated for substantially completing the removal of the fluorescent protecting group.

Typically, the coupling step in which the first amino acid or first peptide is reacted with the α-amine protected second amino acid or second peptide comprises adding a coupling agent.

This invention also relates to coupling agents that are suitable for use in the methods of this invention. Typical coupling agents are selected from the group consisting of carbodiimides and triazoles. Preferred carbodiimides are diisopropylcarbodiimide (DIC), dicyclohexylcarbodiimid (DCC), 1-ethyl-3-(3-dimethylaminopropyl)carbodiimid (EDC), 2-(((ethylimino)methylene)amino)-2-methylpropane-1-sulfonate (ESC) and 2,2'-(methanediylidenebis(azanylylidene))bis(2-methylpropane-1-sulfonate) (DSC). Preferred triazoles are O-benzotriazolyl-N,N,N',N'-tetramethyluronium hexafluorophospate (HBTU), 2-(1H-Benzotriazole-]-yl)-1,1,3,3-tetrantethyluronium tetrafluorobBorate (TBTU), Boc-histidine(tosyl); B01' and B01'-Cl, (benzotriazol-1-yloxy)tripyrrolidinophosphonium hexafluorophosphate (PyBOB), and 1-hydroxybenzotriazole (HOBt).

In a preferred embodiment of the invention, the coupling agent comprises a sulfonic group. The sulfonic group increases the solubility of the coupling agent in water containing solvents and allows for a subsequent separation of the coupling reagent by anion exchange.

Preferred coupling agents are those shown in the following formulae 26 to 30:

General Formula 26

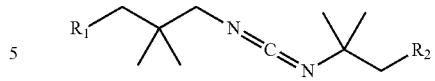

wherein R1 is preferably selected from $SO_3^-$, $OSO_3^-$ ester, $OPO_3^{2-}$ ester, $PO_3^{2-}$, $N(CH_3)_2$, $N(CH_3)_3^+$ and CN, in particular R1 is $SO_3^-$. R2 is preferably selected from $SO_3^-$, $OSO_3^-$ ester, $OPO_3^{2-}$ ester, $PO_3^{2-}$, $N(CH_3)_2$, $N(CH_3)_3^+$ and CN, in particular R2 is $SO_3^-$. R1 and R2 can be the same or different.

General Formula 27

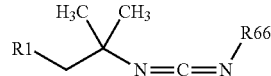

wherein R1 is selected from $SO_3^-$, $PO_3^{2-}$, $OSO_3^-$ ester, $OPO_3^{2-}$ ester, $N(CH_3)_2$, $N(CH_3)_3^+$ and CN, in particular R1 is $SO_3^-$. R66 is preferably selected from short chain alkyl, preferably $C_1$ to $C_8$ alkyl, more preferably $C_1$ to $C_4$ alkyl.

General Formula 28

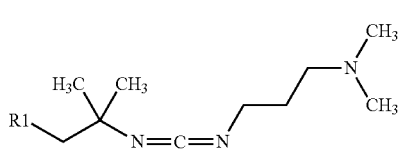

wherein R1 is selected from $SO_3^-$, $PO_3^{2-}$, $OSO_3^-$ ester, $OPO_3^{2-}$ ester, $N(CH_3)_2$, $N(CH_3)_3^+$ and CN, in particular R1 is $SO_3^-$.

General Formula 29

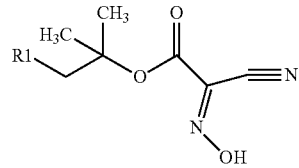

wherein R1 is selected from $SO_3^-$, $OSO_3^-$ ester, $OPO_3^{2-}$ ester, $PO_3^{2-}$, $N(CH_3)_2$, $N(CH_3)_3^+$ and CN, in particular R1 is $SO_3^-$.

General Formula 30

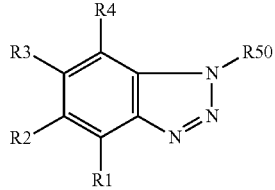

wherein R1 to R4 are independently selected from hydrogen, $SO_3^-$, $OSO_3^-$ ester, $OPO_3^{2-}$ ester, $PO_3^{2-}$, $N(CH_3)_2$, $N(CH_3)_3^+$ and CN with the proviso that at least one, preferably at least two of R1 to R4 are selected from $SO_3^-$, $OSO_3^-$ ester, $OPO_3^{2-}$ ester, $PO_3^{2-}$, $N(CH_3)_2$, $N(CH_3)_3^+$ and CN. In preferred embodiments all of R1 to R4 that are not $SO_3^-$, $PO_3^{2-}$, $OSO_3^-$ ester, $OPO_3^{2-}$ ester, $N(CH_3)_2$, $N(CH_3)_3^+$ or CN are hydrogen.

In preferred embodiments R3 is selected from $SO_3^-$, $OSO_3^-$ ester, $OPO_3^{2-}$ ester, $PO_3^{2-}$, $N(CH_3)_2$, $N(CH_3)_3^+$ and CN, in particular R3 is $SO_3^-$. Preferably, R1, R2, R4 and R5 are hydrogen.

In preferred embodiments, R50 is selected from one or more of hydroxyl or one of the substituents given in formulas 30.1 to 30.4 below, wherein B denotes the structure of General Formula 30:

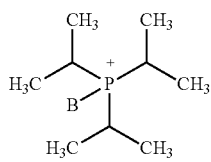

Formula 30.1

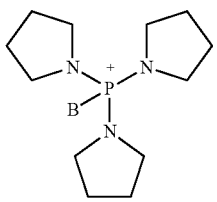

Formula 30.2

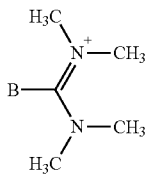

Formula 30.3

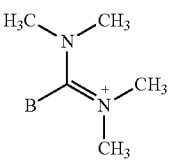

Formula 30.4

Particularly preferred coupling agents are selected from the group consisting of 2-(((ethylimino)methylene)amino)-2-methylpropane-1-sulfonate (ESC), 2,2'-(methanediylidenebis(azanylylidene))bis(2-methylpropane-1-sulfonate) (DSC), 2-((((3-(dimethylamino)propyl)imino)methylene) amino)-2-methylpropane-1-sulfonate (MPSC), and are N-hydroxysulfosuccinimide (Sulfo-NHS) and 2-(2-cyano-2-(hydroxyimino)acetoxy)-2-methylpropane-1-sulfonate (Cyms).

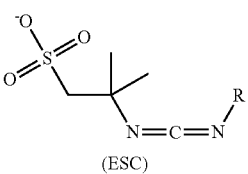

Formula 31

(ESC)

R = Me, Et, ...

wherein R is selected from $C_1$ to $C_8$ alkyl, preferably $C_1$ to $C_4$ alkyl.

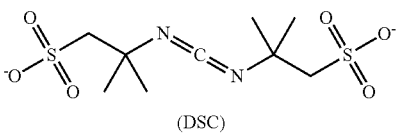

Formula 32

(DSC)

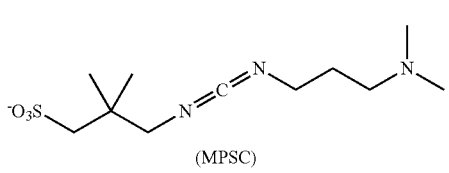

Formula 33

(MPSC)

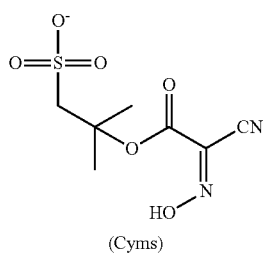

Formula 34

(Cyms)

The coupling step may further comprise adding a capping reagent. The capping agents described and their use for capping free amines in a method of peptide synthesis form an independent part of the present invention. The capping agents may be used in the method of this invention but they may also be used in other methods of peptide synthesis. The capping agents have the benefit of facilitating easy, secure and cost-effective purification of the resulting product compositions. The capping reagent allows capping of free amines after the coupling steps in order to prevent the formation of side products, wherein the capping agent comprises I. a backbone structure,
II. at least one water-solubility enhancing functional group and
III. at least one reactive group,
  wherein backbone structure comprises a moiety selected from the group selected from short chain alkyl, preferably $C_1$ to $C_8$ alkyl, cyclic alkyl chains or aromatic compounds, more preferably $C_1$ to $C_4$ alkyl or benzyl,
  wherein the water-solubility enhancing functional group is selected from the group consisting of $SO_3^-$, $PO_3^{2-}$, $OSO_3^-$ ester, $OPO_3^{2-}$ ester, $N(CH_3)_2$, $N(CH_3)_3^+$, CN and combinations thereof, and
  wherein the water-solubility enhancing functional group and the reactive group are attached to the backbone structure via at least one covalent bond.

The reactive group is preferably selected from the group consisting of carboxylic acid, carboxylic acid halogenide, carboxylic acid O-succinimide, carboxylic acid Oxyma ester, carboxylic acid anhydride, halogenide, and thiol groups.

In an embodiment of this invention the capping agents are added in a method of peptide synthesis according to this invention. In an alternative embodiment, the capping agents are added in an alternative method of peptide synthesis, which alternative method comprises the steps of reacting a first amino acid or a first peptide with an α-amine protected second amino acid or second peptide in a solvent and removing the α-amine protecting group with a deprotecting solution, characterized in that a capping agent is added to the reaction mixture for capping free amines. The capping agents are selected from those mentioned above. After the completion of the reaction the reaction mixture is passed through an affinity column in order to purify the reaction mixture. The affinity column is preferably selected from an anion or cation exchange column.

The water solubility enhancing functional group allows an easy purification after coupling. In a preferred embodiment of the invention, the capping reagent comprises a sulfonic group.

Preferred capping reagents are 2-sulfoacetic acid or 4-sulfobenzoic acid.

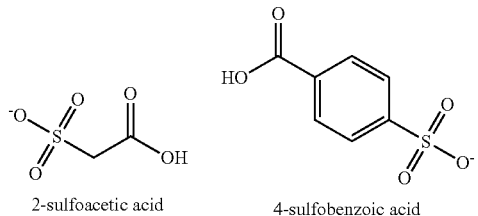

In another preferred embodiment of the invention, the method further comprises at least one washing step using a solvent selected from the group consisting of water, alcohol, and a mixture of water and alcohol, and a step of collecting waste solutions obtained in the washing steps, contacting the waste solutions to an affinity chromatography column, preferably a solid anion and/or cation exchange support, thereby retaining waste compounds that a water solubility enhancing functional group, particular a charged functional group like $SO_3^-$, $OSO_3^-$ ester, $OPO_3^{2-}$ ester, $PO_3^{2-}$, and $N(CH_3)_3^+$. It has been particularly effective to use an anion exchange support for removal of compounds that contain at least one sulfonic group. Subsequently, the waste compounds may be collected by regeneration of the affinity chromatography column, preferably a solid anion and/or cation exchange support, and disposed. Alternatively, the affinity chromatography column, preferably a anion and/or cation exchange support material, containing the waste compounds may be disposed.

Washing steps are typically carried out after the coupling step and after the deprotection step. The anion and/or cation exchange step allows for removing all sulfo-containing compounds, such as unreacted or cleaved protecting groups and reagents, e.g. coupling agents and capping reagents as described herein from the washing solutions. The waste compounds are retained on the anion or cation exchange column and a purified solvent is obtained. The retained compounds can be disposed together with the anion or cation exchange material or after elution and only a minimum amount of chemical waste has to be disposed.

In a further preferred embodiment of the invention, the method further comprises a purification step after the cleaving step wherein the solution containing the deprotected and cleaved target protein or peptide is contacted to an affinity chromatography column, preferably a solid anion and/or cation exchange support, thereby retaining waste compounds such as those comprising a sulfonic group, and collecting the purified target protein. In preferred embodiments the waste compounds comprise at least one sulfonic group as part of the protecting groups and other reagents. Due to the sulfo-containing protecting groups, and the sulfo-containing reagents it is possible to remove substantially all of the excess chemicals and side products generated during the coupling, the deprotection and the cleaving reactions in a solvent selected from the group consisting of water, alcohol, and mixtures of water and alcohol by affinity chromatography column, preferably ion exchange methods. Of course, this also works with the other charged functional groups. Only the target peptide is able to run through the ion exchange column whereas the peptide side products, protection group residues and excess reagents are retained on the column. After regeneration of the column, only a minimum amount of chemical waste has to be disposed. This is a beneficial effect of using charged functional groups such as $SO_3^-$, $OSO_3^-$ ester, $OPO_3^{2-}$ ester, $PO_3^{2-}$, and $N(CH_3)_3^+$. But even if one or more of the uncharged functional groups are used, the process can still be carried out in water, thereby reducing the amount of waste chemicals compared to prior art processes.

A preferred aspect of the present invention relates to a protecting reagent selected from the group consisting of 9-(3,6-disulfo)fluorenylmethyloxy-carbonyl halogenides (Smoc halogenide), 9-(3,6-disulfo)fluorenylmethyloxy-carbonyl N-hydroxysuccinimid (Smoc-NHS), 9-(3,6-disulfo)fluorenylmethyloxy-carbonyl O-succinimide (Smoc OSu), 9-(2,7-disulfo)fluorenylmethyloxy-carbonyl halogenides (Smoc halogenide), 9-(2,7-disulfo)fluorenylmethyloxy-carbonyl N-hydroxysuccinimid (Smoc-NHS), 9-(2,7-disulfo) fluorenylmethyloxy-carbonyl O-succinimide (Smoc OSu), tri(4-sulfophenyl)methyl halogenides (SulfoTrt halogenide), tert-butyl-(2-sulfonate)oxycarbonyl anhydride (Sboc$_2$O), tert-butyl-(2-sulfonate)oxycarbonyl 0-succinimide (Sboc-OSu), 4-sulfo-carbobenzyloxy halogenides (SulfoCBz halogenide), 2-hydroxy-2-methylpropane-1-sulfonate (tBuS), 2-bromo-2-methylpropane-1-sulfonate (tBuS), 2-mercapto-2-methylpropane-1-sulfonate (StBuS), 4-sulfobenzyl halogenides (BzS halogenide), and 4-sulfo-benzyloxymethyl halogenides (BOMS halogenide).

Preferred halogenides according to this invention are chloride and bromide. The above compounds are useful reagents for protecting a functional group, e.g. an amine group, an alcohol group, a thiol group, or a carboxyl group in a chemical reaction in organic chemistry.

Another aspect of the present invention relates to modified amino acids, peptides and salts thereof comprising a protecting group selected from the group consisting of those shown above under formulae 6 to 25, more preferably selected from those shown above under formulae 6 to 10. In particularly preferred embodiments these protecting groups include 9-(3,6-disulfo)fluorenylmethyloxy-carbonyl, 9-(2,7-disulfo)fluorenylmethyloxy-carbonyl group, tri(4-sulfophenyl)methyl group (SulfoTrt), tert-butyl-(2-sulfonate)oxycarbonyl group (Sboc), 4-sulfo-carbobenzyloxy group (SulfoCBz), tert-butyl-1-sulfonate group (tBuS), 1-sulfo-2-methyl-2-propanethiol group (StBuS), 4-sulfobenzyl group (BzS), and 4-sulfo-benzyloxymethyl group (BOMS).

A further aspect of the invention relates to an apparatus for carrying out a method for solid phase synthesis of peptides. Said apparatus comprises a reaction vessel for receiving an insoluble (e.g. polymeric) support material and a fluorimeter arranged for monitoring the changes in fluorescence intensity that is generated by a protecting group coupled to the insoluble support material. Due to the intrinsic fluorescence of the protecting agents of this invention (e.g. Smoc), a quantitative analysis of fluorescence intensity of the insoluble support material gives information about the progress of the coupling reaction or the deprotection reaction in above mentioned SPPS method. The integration of the fluorimeter into a peptide synthesis apparatus allows for accelerated automated synthesis.

In a preferred embodiment of the invention, the apparatus further comprises at least one solid anion and/or cation exchange support arranged for separating waste compounds. The solid anion and/or cation exchange support may be arranged within the product stream in order to separate the target protein from waste compounds, such as the sulfo-containing peptide side products, protection group residues and excess reagents. Alternatively or additionally a solid anion exchange support may be arranged within the waste stream in order to separate waste compounds, such as excess reagents and side products from washing solutions obtained after the coupling and deprotection steps.

The invention will be further described, by way of illustration, with reference to the accompanying drawing in which FIG. 1 is a schematic illustration of an apparatus according to the present invention.

FIG. 1 illustrates schematically the overall layout of automatic solid phase peptide synthesizer apparatus for use in carrying out a preferred method as described above. The apparatus comprises a reaction vessel 1 containing a first amino acid or a first peptide anchored to an insoluble polymeric support, a reagent container 2 including multiple reservoirs for providing coupling reagents, capping reagents, cleaving reagents etc., a solvent container 3, and an amino acids and/or peptide container 4 including multiple reservoirs for providing protected amino acids and/or peptides.

The reaction vessel 1 and the containers 2, 3, 4 are connected via tubes and valves arranged in such a way that specified quantities of specified reagents, amino acids and/or peptides can be delivered to the reaction vessel 1 in a specified sequence under control of control means (not shown) in a conventional manner.

The apparatus includes a fluorimeter 5 which is arranged for measuring monitoring the changes in fluorescence intensity of the contents of the reaction vessel 1. It is understood that alternatively, the reaction vessel 1 can comprise an integrated fluorimeter 5.

The reaction vessel is equipped with a waste outlet 6 for removing the waste stream after each washing step and a product outlet 7 for removing the product stream after the cleavage step. The waste outlet 6 is connected via a waste tube 8 to a chamber 9 where the pH of the stream is adjusted for subsequent separation and to a first ion exchange column 10. The product outlet 7 is connected via a product tube 11 to a second ion exchange column 12.

The ion exchange columns 10, 11 are arranged for retaining sulfonated waste compounds, such as side products, excess reagents and protection group residues that subsequently must be disposed. The purified solvent stream from the first ion exchange column 10 can be conducted to the sewer system or recycled. The purified product stream from the second ion exchange column 12 is used for obtaining the target protein.

The invention is illustrated but not limited by the following examples.

EXAMPLES

Example 1: Synthesis of 9-(3,6-disulfo)fluorenylmethyloxycarbonyl chloride (Smoc-Cl)

2 g (7.73 mmol) of Fmoc-chloride was treated with 20 mL of concentrated sulfuric acid.

After work up of the reaction mixture 2.96 g (7.07 mmol, 91.4%) of crude Smoc-chloride was obtained in form of a slightly yellow solid.

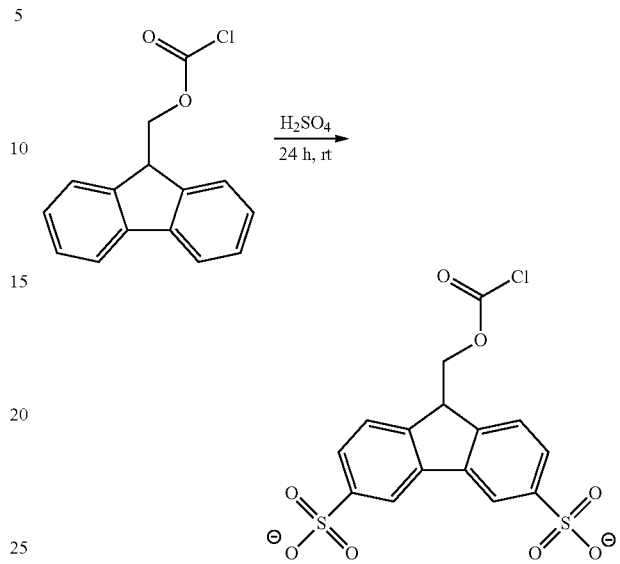

Analytical Data of Smoc-Chloride:

$^1$H NMR (500 MHz, D$_2$O) δ=7.80 (s, 2H), 7.69 (d, J=7.9 Hz, 2H), 7.48 (d, J=7.8 Hz, 2H), 3.84 (d, J=4.8 Hz, 2H), 3.45 (t, J=4.7 Hz, 1H).

$^{13}$C NMR (126 MHz, D$_2$O) δ=145.57, 142.54, 141.65, 125.16, 121.61, 120.90, 62.54, 49.65.

Example 2: Synthesis of 9-(2,7-disulfo)fluorenylmethyloxycarbonyl chloride (Smoc-Cl)

2 g (7.73 mmol) of Fmoc-chloride were treated with 20 mL of concentrated sulfuric acid and heated to 100° C. Sulfuric acid was neutralised with NaOH (pH9.5) and solvent removed under reduced pressure and NMR analytics confirmed formation of target intermediate. The intermediate was dissolved again in 20% sulfuric acid in water, stirred for 6 h to form 9-(2,7-disulfo)fluorenylmethanol. Sulfuric acid was neutralised with NaOH (pH 6.7) and the solvent removed under reduced pressure. A solution of 1.2 eq. phosgene in 25 ml of DCM was cooled to 0° C. and 9-(2,7-disulfo)fluorenylmethanol was added slowly under stirring (Carpino and Han, *The Journal of Organic Chemistry* 1972, 37, (22), 3404-3409). The solution was stirred for 1 h in the ice bath and then let stand for 4 h at ice-bath temperature. Solvent and excess phosgene were removed under reduced pressure giving the corresponding product.

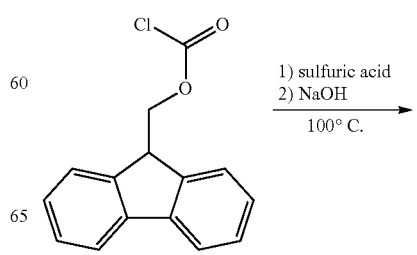

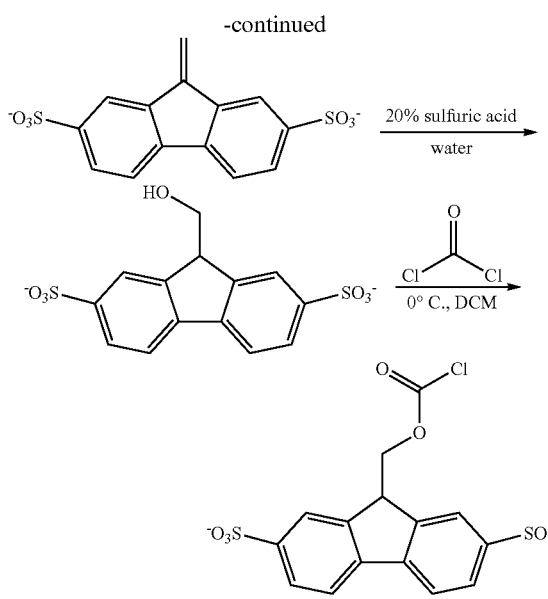

NMR Intermediate:
$^1$H NMR (300 MHz, D$_2$O) δ: 6.09 (s, 2H), 7.23-7.40 (m, 2H), 7.72 (s, 2H), 7.95 (d, J=6.2 Hz, 2H).
$^{13}$C NMR (75 MHz, D$_2$O) δ: 142.61, 132.99, 131.74, 130.23, 129.28, 127.22, 125.57, 124.69.
LC-APCI-MS for 9-(2,7-disulfo)-fluorenylmethyloxycarbonyl chloride:
LC-APCI-MS calculated for C$_{15}$H$_9$ClO$_{22}$. m/z: 256.03. Measured m/z: 256.94 [M−H−2×SO$_3$]$^-$.

Example 3: Synthesis of Smoc-Gly-OH (Smoc-Glycine)

2.5 g (8.41 mmol) of Fmoc-glycine were treated with 30 mL of concentrated sulfuric acid. After work up of the reaction mixture 3.7 g (8.09 mmol, 96.2%) of crude Smoc-glycine was obtained in form of a slightly yellow powder.

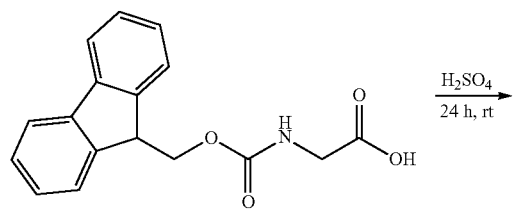

Analytical Data of Smoc-Glycine:
LC-APCI-MS calculated for C$_{17}$H$_{14}$NO$_{10}$S$_2^-$ m/z: 456.01. Measured m/z: 455.85 [M−H]$^-$.

$^1$H NMR (500 MHz, D$_2$O) δ=8.01 (s, 2H), 7.87 (d, J=7.9 Hz, 2H), 7.79 (d, J=8.0 Hz, 2H), 5.95 (s, NH), 4.41 (d, J=6.2 Hz, 2H), 4.01 (t, J=6.2 Hz, 1H), 3.67 (s, 2H).
$^{13}$C NMR (126 MHz, D$_2$O) δ=158.21, 144.94, 142.41, 141.88, 125.51, 122.09, 121.09, 65.75, 46.95, 44.39.

Example 4: Synthesis of Smoc-L-Ala-OH (Smoc-Alanine)

2.5 g (8.03 mmol) of Fmoc-L-alanine were treated with 30 mL of concentrated sulfuric acid. After work up of the reaction mixture 3.8 g (7.64 mmol, 95.1%) of crude Smoc-L-alanine was obtained in form of a white powder.

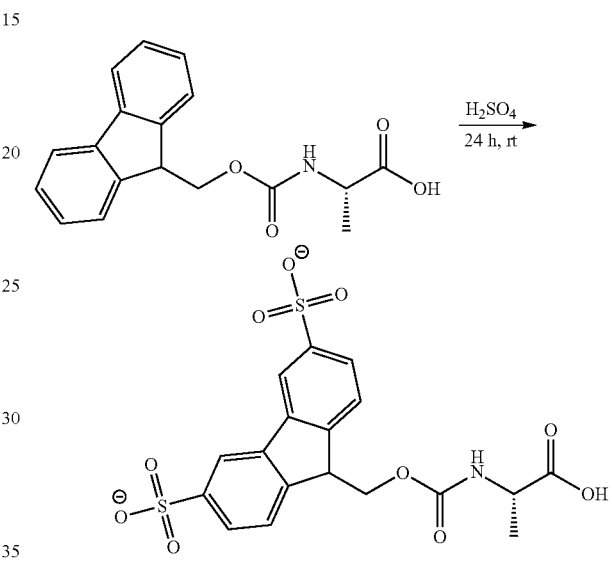

Analytical Data of Smoc-Alanine:
LC-APCI-MS calculated for C$_{18}$H$_{18}$NO$_7$S. m/z: 390.06. Measured m/z: 389.96 [M−HSO$_3$]$^-$.
$^1$H NMR (500 MHz, MeOD) δ=7.78 (d, J=19.6 Hz, 2H), 7.57 (d, J=8.1 Hz, 2H), 7.55 (dd, 2H), 5.94 (s, NH), 3.95 (m, OH+2H), 3.85 (q, J=7.4 Hz, 1H), 2.93 (t, J=1.64 Hz, 1H), 1.01 (d, J=7.3 Hz, 3H).
$^{13}$C NMR (126 MHz, MeOD) δ=175.11, 158.10, 146.21, 145.89, 145.44, 143.54, 127.09, 124.04, 123.90, 121.40, 67.23, 51.05, 48.51, 17.58.

Example 5: Synthesis of Smoc-L-Ile-OH (Smoc-Isoleucine)

2.5 g (7.07 mmol) of Fmoc-L-isoleucine were treated with 30 mL of concentrated sulfuric acid. After work up of the reaction mixture 3.8 g (6.82 mmol, 96.4%) of crude Smoc-L-isoleucine was obtained in form of a white powder.

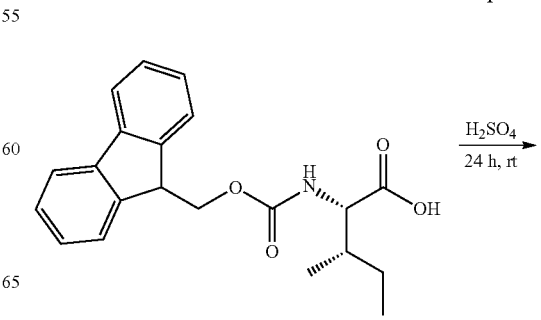

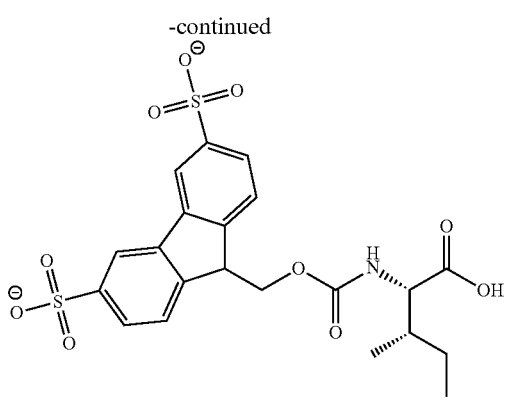

Analytical Data of Smoc-Isoleucine:

LC-APCI-MS calculated for $C_{21}H_{22}NO_7S$. m/z: 432.11. Measured m/z: 432.06 [M−$HSO_3$]⁻.

$^1$H NMR (500 MHz, MeOD) δ=7.79 (d, J=16.5 Hz, 2H), 7.57 (d, J=8.0 Hz, 2H), 7.55 (dd, J=8.0, 1.5 Hz, 2H), 4.15-3.89 (m, OH+2H), 3.77 (d, J=6.2 Hz, 1H), 2.93 (t, J=1.6 Hz, 1H), 1.50 (dtd, J=13.2, 10.1, 6.7 Hz, 1H), 1.20-1.05 (m, 1H), 0.97-0.81 (m, 1H), 0.55 (d, J=6.86 Hz, 3H), 0.54 (t, J=7.43 Hz, 3H).

$^{13}$C NMR (126 MHz, MeOD) δ=173.98, 158.49, 146.15, 145.45, 143.48, 127.09, 124.02, 123.95, 121.38, 67.33, 60.30, 48.55, 38.31, 26.30, 15.98, 11.66.

Example 6: Synthesis of Smoc-L-Leu-OH (Smoc-Leucine)

2.5 g (7.07 mmol) of Fmoc-L-leucine were treated with 30 mL of concentrated sulfuric acid. After work up of the reaction mixture 3.6 g (7.01 mmol, 99.1%) of crude Smoc-L-leucine was be obtained in form of a white powder.

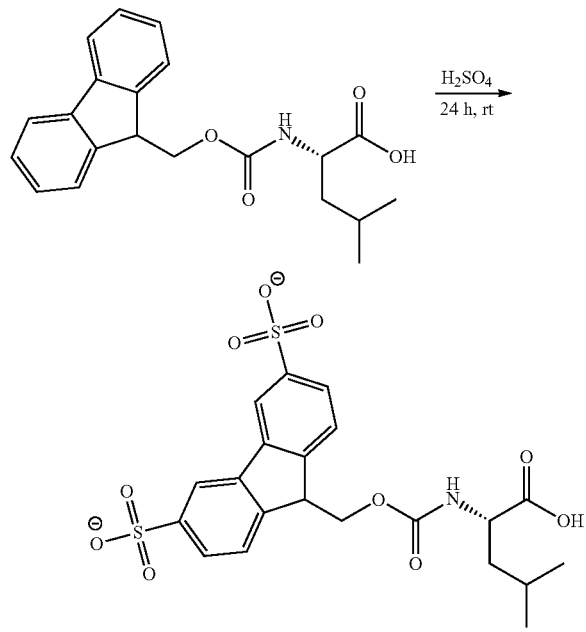

Analytical Data of Smoc-Leucine:

LC-APCI-MS calculated for $C_{21}H_{22}NO_7S$. m/z: 432.11. Measured m/z: 432.06 [M−$HSO_3$]⁻.

$^1$H NMR (500 MHz, MeOD) δ=7.80 (d, J=18.0 Hz, 2H), 7.58 (d, J=8.1 Hz, 2H), 7.57 (dd, J=8.3, 4.1 Hz 2H), 4.11-3.93 (m, OH+2H), 3.86 (dd, J=9.9, 5.3 Hz, 1H), 2.94 (t, 1H), 1.41-1.31 (m, 1H), 1.30-1.17 (m, 2H), 0.57 (dd, J=14.7, 6.5 Hz, 6H).

$^{13}$C NMR (126 MHz, MeOD) δ=175.08, 158.41, 146.18, 145.95, 145.38, 143.52, 127.10, 124.07, 123.97, 121.40, 67.27, 53.99, 48.54, 41.47, 25.86, 23.27, 21.78.

Example 7: Synthesis of Sulfo-Trt

In a heated out round bottom flask under nitrogen atmosphere, 237 mg (9.75 mmol, 3.0 eq.) magnesium were suspended in 10 mL THF. To this mixture ¹/₁₀ of a solution of 1.878 g (9.75 mmol, 3 eq.) 4-chlorobenzenesulfonic acid in 15 mL THF was added under vicious steering. To start the Grignard reaction, the mixture was heated to reflux and a drop of bromine was added. Afterwards the remaining part of the 4-chlorobenzenesulfonic acid solution was added dropwise and the mixture was refluxed for an additional 30 minutes before allowed to cool to room temperature.

In a second step, Kochi's coupling method was employed. For this purpose, a three neck flask was put under nitrogen atmosphere and cooled to −78° C. by using a suspension of dry ice in methanol. Afterwards 50 mL of THF were added, followed by 0.361 mL (3.25 mmol, 1 eq.) carbon tetrachloride and 0.325 ml (0.03 mmol, 0.01 eq., 0.1 mol/L solution in THF) dilithium tetrachlorocuprate(II). To this solution the previously prepared Grignard reagent was added dropwise. After stirring for 1 h at −78° C. and 6 h at 0° C., the mixture was allowed to warm to room temperature and stirred for an additional 18 h. The solution was quenched by adding 20 mL of water. Volatile components were removed under reduced pressure, resulting in 1.69 g of crude 4,4',4"-(hydroxymethanetriyl)tribenzenesulfonate (Sulfo-Trt), in form of a brown solid. The product was isolated by semi-preparative RP-HPLC. Treating of 4,4',4"-(hydroxymethanetriyl)tribenzenesulfonate with thionyl chloride ($SOCl_2$) leaded to formation of tri(4-sulfophenyl)methyl chloride (Sulfo-Trt chloride). The solvent was removed under reduced pressure.

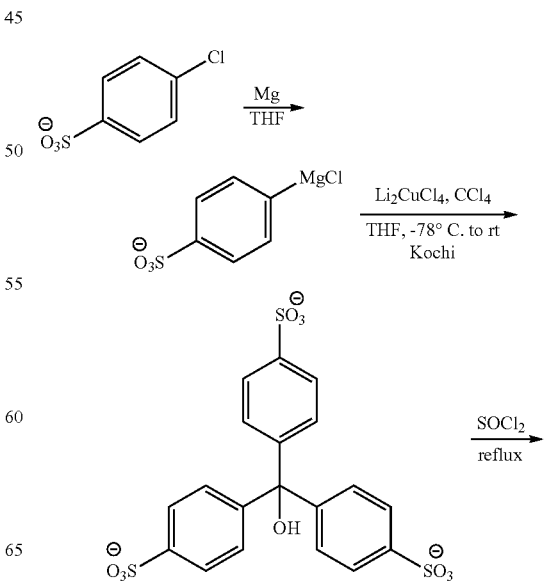

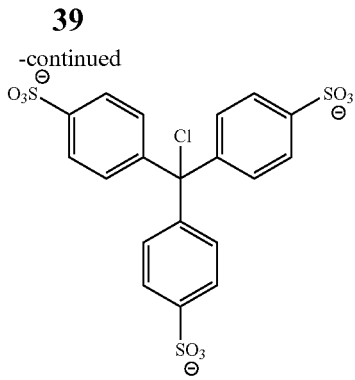

Analytical Data of Sulfo-Trt:
$^1$H NMR (500 MHz, D$_2$O) δ=7.68 (d, J=8.6 Hz, 6H), 7.44 (d, J=8.6 Hz, 6H).
$^{13}$C NMR (126 MHz, D$_2$O) δ=140.99, 136.88, 128.96, 127.02, 75.45.

Example 8: Synthesis of 2-hydroxy-2-methylpropane-1-sulfonate (tBuS-OH)

6.00 g 2-methyl-2-propen-1-sulfonic acid sodium salt was diluted in 50 ml water. 10 ml sulfuric acid was added and the reaction stirred at room temperature overnight. Sulfuric acid was removed by CaCO$_3$ precipitation. The solvent was removed by reduced pressure. The product was obtained as white powder. LC-MS and NMR analytics confirmed target compound.

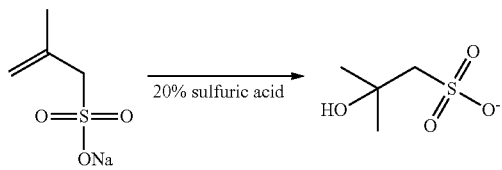

Analytical Data of tBuS-OH:
ESI-MS calculated for C$_4$H$_9$O$_4$S$^-$ m/z: 153.18, measured m/z: 152.9[M−H]$^-$.
$^1$H NMR (500 MHz, DMSO-d$_6$) δ: 1.18 (s, 6H), 2.67 (s, 2H), 5.20 (s, 1H).
$^{13}$C NMR (126 MHz, DMSO) δ: 67.84, 61.81, 39.52, 29.65.

Example 9: Synthesis of 2-bromo-2-methylpropane-1-sulfonate (tBuS-Br)

6.00 g 2-methyl-2-propen-1-sulfonic acid sodium salt was diluted in 20 ml HBr (48% w/w). The solvent was removed under reduced pressure. The product was obtained as a whitebrown powder. LC-MS and NMR analytics confirmed target compound.

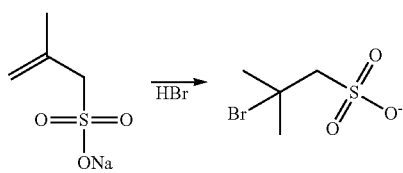

Analytical Data of tBuS-Br:
ESI-MS calculated for C$_4$H$_8$BrO$_3$S$^-$ m/z: 216.07, measured m/z: 216.8[M−H]$^-$.

Example 10: Synthesis of 2-mercapto-2-methylpropane-1-sulfonate (StBuS)

3.00 g 2-methyl-2-propen-1-sulfonic acid sodium salt were diluted in 25 ml HCl conc. and the reaction solution stirred overnight. Afterwards the acid was neutralised with NaOH (pH=6.8) and the solvent was removed by reduced pressure. In a heated out round bottom flask under nitrogen atmosphere, 233.67 mg magnesium were suspended in 20 mL THF. A suspension of 1.5 g tBuS-Cl in 15 mL THF was added under vicious steering. To start the Grignard reaction, the mixture was heated to reflux (70° C.) and a drop of bromine was added and the mixture was refluxed for additional 90 minutes before allowed to cool to room temperature. 4 eq. sulphur was added to the Grignard reagent and stirred for 8 h. Afterwards 200 ml water were added. The mixture was stirred for 2 h at room temperature. Subsequently, the solvent was removed under reduced pressure and the resulting white powder was analysed by NMR.

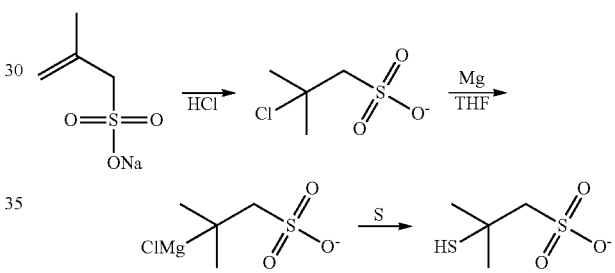

Analytical Data of StBuS:
$^1$H NMR (500 MHz, Deuterium Oxide) δ: 1.56 (s, 6H), 2.18 (s, J=1.3 Hz, 1H), 3.67 (s, 2H).
$^{13}$C NMR (126 MHz, D$_2$O) δ: 61.66, 32.13, 28.48.

Example 11: Synthesis of (9-BBN)-Lys(SBoc)

1.68 g Lysine was suspended in dry THF and 24.28 ml 9-Borabicyclo(3.3.1)nonan (9-BBN) in THF (0.5 mol/L) was added under inert gas. The resulting suspension was refluxed for 18 h at 100° C. The solvent was removed under reduced pressure. (9-BBN)-Lys was diluted in 20 ml THF and 1.97 g 1,1'-carbonyldiimidazole and 2.54 g tBuS-OH was added under inert gas. The resulting solution was stirred for 5 h. The solvent was removed under reduced pressure and the resulting crude product was washed tree times with DCM to remove imidazole residues.

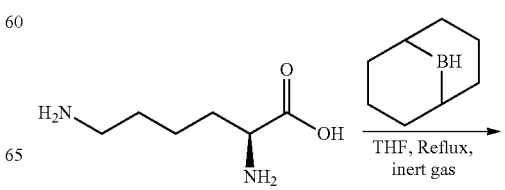

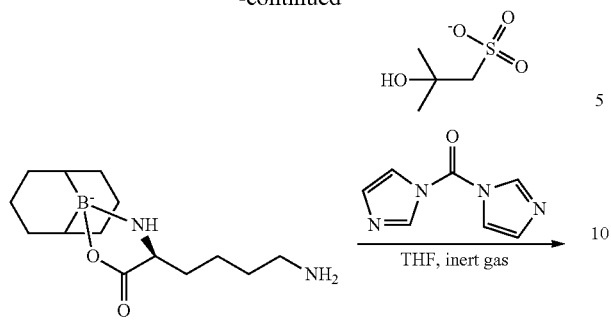

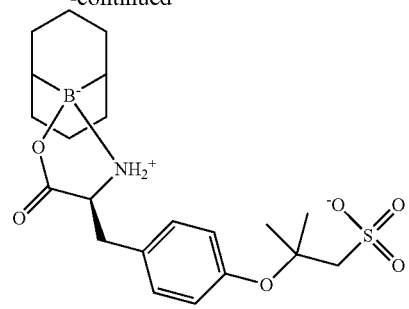

Analytical Data of (9-BBN)-Lys(SBoc):

ESI-MS calculated for $C_{19}H_{33}BN_2O_7S^{2-}$ m/z: 444.35, measured m/z: 443.2[M–H]⁻.

Example 12: Synthesis of (9-BBN)-Tyr(tBus)

2.00 g tyrosine was suspended in dry THF and 25 ml 9-BBN in THF (0.5 mol/L) was added under inert gas. The resulting suspension was refluxed for 18 h at 100° C. The solvent was removed under reduced pressure. (9-BBN)Tyr was suspended in 20 ml THF and 2.39 g tBuS-Br was added under inert gas. The resulting solution was stirred for 2 d. The solvent was removed under reduced pressure and the resulting crude product washed tree times with THF to remove bromide residues.

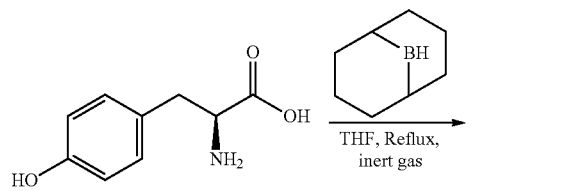

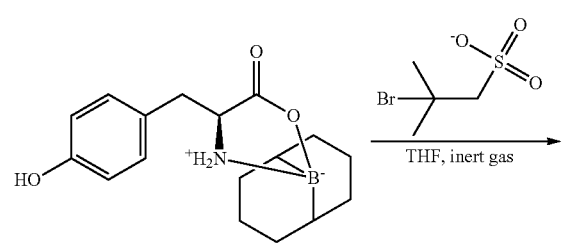

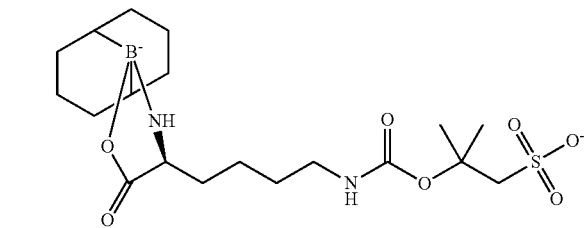

Analytical Data of (9-BBN)-Tyr(tBuS):

ESI-MS calculated for $C_{21}H_{31}BNO_6S^-$ m/z: 436.35, measured m/z: 436.2[M+H]⁺, 453.2[M+H₂O]⁺.

Example 13: Stability Test of Smoc-Protected Amino Acids

To determine the stability of Smoc-protected amino acids in an aqueous environment, Smoc-glycine and Smoc-L-leucine were dissolved in water and incubated at ambient temperature for eight days. The condition of the amino acids was checked after 3, 6 and 8 days using analytical RP-HPLC. The compounds had to be stable in aqueous environment for a considerable amount of time. To prove this stability, Smoc-glycine and Smoc-leucine were dissolved in a minimal amount of water and kept at ambient temperature. The results of the experiments were monitored by RP-HPLC, performed after 3, 6 and 8 days. As a result, no significant change in the composition of the amino acids was observed.

Example 14: N-Terminal Deprotection of Smoc-Protected Amino Acids

For the usage in SPPS, protective groups must be easily and efficiently deprotectable under safe conditions. To determine the deprotection conditions of Smoc-protected amino acids, a series of experiments were performed by dissolving 1 mg of Smoc-glycine in 1 mL of water or ethanol. To this solution, the one of the following bases ammonia (10% aq.),
ethanolamine (50% aq.),
ethylendiamine (50% aq.) or
piperidine (50% aq.)

was added and the mixture was incubated under shaking for 5 min at room temperature. The result was analysed by analytical RP-HPLC and ESI-MS.

The results showed that solutions of ammonia or amine in water are sufficient for Smoc deprotection at room temperature.

Additionally to piperidine which is the standard base used in Fmoc-SPPS deprotection appeared possible using water-soluble bases, such as ammonia, ethanolamine, and ethylenediamine. This allows access to significantly cheaper and easier procedures compared to the piperidine-based deprotection.

Example 15: Purification by Affinity Chromatography

Smoc-alanine was mixed with unprotected alanine as an artificial impurity, dissolved in 1M formic acid and loaded to a DEAE Sephadex A-25 ion exchange column. After washing the column with additional formic acid, the Smoc-alanine was eluted with a 4M solution of ammonium formate. The solution before loading, the solution after loading and the eluated fraction were analysed by RP-HPLC.

The results show that unprotected alanine passed the ion exchange column unhindered while the Smoc-protected alanine bound to the column. With the change of the mobile phase to a 4M solution of ammonium formate, the Smoc-alanine was eluted from the column without any impurity remaining. Thereby it has been shown that the Smoc-group can be successfully used in affinity chromatography for purification purposes.

Example 16: Synthesis of the Test Peptide H-V-G-G-V-G-OH Following the Smoc Approach Couplings of Smoc-protected amino acids were performed as follows. Thus, 3 eq. of the respective Smoc-protected amino acid, 2.8 eq. of the activator 1-ethyl-3-(3-dimethylaminopropyl)carbodiimide (EDC), 3.0 eq N-hydroxysuccinimide (NHS) and 6 eq. of sodium hydrogen carbonate as a general base were dissolved in a minimal amount of water and preactivated for 3 min. A typical coupling took 60 min at ambient temperature. N-terminal deprotection of a peptide resin was performed as double deprotection step with 10% aq. ammonia. After cleavage from the support, the test peptide was analysed by RP-HPLC and ESI-MS.

Analytical Data of the Peptide H-V-G-G-V-G-OH:
RP-HPLC, 10→60% MeCN, $t_R$=19.1 min.
ESI-MS calc. for $C_{16}H_{29}N_5O_6$ m/z: 387.21 meas. 387.0 $[M+H]^+$ wherein the at least two water-solubility enhancing functional groups are selected from $SO_3^-$, $PO_3^{2-}$, $N(CH_3)_2$, $N(CH_3)_3^+$, CN, $OSO_3^-$ ester, $OPO_3^{2-}$ ester and combinations thereof, and wherein the water-solubility enhancing functional group and the reactive group are attached to the backbone structure via at least one covalent bond, for protecting a functional group in a water-based reaction of a first amino acid or first peptide with an α-amine protected second amino acid or α-amine protected second peptide, wherein the protective agent forms protecting groups on at least one of said α-amino functional group during the water-based reaction of said first amino acid or first peptide with said α-amine protected second amino acid or α-amine protected second peptide, and wherein the C-terminus of said first amino acid or first peptide is anchored to an insoluble support.

2. The method according to claim 1, wherein the functional group to be protected is further selected from amine, alcohol, thiol and carboxyl groups.

3. The method according to claim 2, wherein the reactive group is selected from the group consisting of oxycarbonyl halogenide, oxycarbonyl Oxyma ester, oxycarbonyl O-succinimide, oxycarbonyl anhydride, halogenide, hydroxide and thiol groups.

4. The method according to claim 3, wherein the water solubility-enhancing functional group is $SO_3^-$.

5. Protective agent suitable for forming protecting groups on functional groups on a peptide and/or amino acid during water based peptide synthesis,

TABLE 1

Fluorescence-monitored SPPS of peptide H-L-V-A-I-G-OH

|  | Water | PEGA resin | Smoc-Gly-PEGA 0.05 mM | Smoc deprot. | Smoc-Ile-PEGA 0.05 mM | Smoc deprot. | Smoc-Ala-PEGA 0.05 mM | Smoc deprot. | Smoc-Val-PEGA 0.05 mM | Smoc deprot. | Smoc-Leu-PEGA 0.05 mM | Smoc deprot. |
|---|---|---|---|---|---|---|---|---|---|---|---|---|
| 1 | 3 | 108 | 1498 | 258 | 1964 | 362 | 1814 | 326 | 1422 | 345 | 1392 | 331 |
| 2 | 3 | 106 | 1670 | 237 | 1933 | 389 | 2117 | 478 | 1386 | 467 | 1350 | 345 |
| 3 | 2 | 99 | 1812 | 284 | 2186 | 384 | 1925 | 346 | 1549 | 346 | 1344 | 365 |
| mean value | 2.67 | 104.33 | 1660.00 | 259.67 | 2027.67 | 378.33 | 1952.00 | 383.33 | 1452.33 | 386.00 | 1362.00 | 347.00 |
| standard deviation | 0.58 | 4.73 | 157.24 | 23.54 | 137.99 | 14.36 | 153.29 | 82.59 | 85.63 | 70.15 | 26.15 | 17.09 |

The fluorescence of water, solid support (PEGA resin) and PEGA resin-peptide was determined after each coupling step and the following deprotection steps. The results are shown in Table 1. Thus, after each coupling step, the fluorescence value rises due to the coupled Smoc group, and after each deprotection steps the fluorescence value decreases again revealing that real-time monitoring of reaction progress is possible.

The invention claimed is:

1. A method of forming protecting groups on functional groups during water-based peptide synthesis, the method comprising using a protective agent,
   wherein the protective agent comprises
   a) a backbone structure,
   b) at least two water-solubility enhancing functional groups and
   c) at least one reactive group,
   wherein the backbone structure comprises a moiety selected from the group consisting of 9-methylfluorene, and/or di- or triphenylmethane, wherein the protective agent comprises
a) a backbone structure,
b) at least two water-solubility enhancing functional group and
c) at least one reactive group,
wherein the backbone structure comprises a moiety selected from the group consisting of 9-methylfluorene, t-butane and/or mono-, di or triphenylmethane, wherein the water-solubility enhancing functional group is selected from the group consisting of $SO_3^-$, $PO_3^{2-}$, $N(CH_3)_2$, $N(CH_3)_3^+$, CN, $OSO_3^-$ ester, $OPO_3^{2-}$ ester and combinations thereof, and wherein the water-solubility enhancing functional group and the reactive group are attached to the backbone structure via at least one covalent bond.

6. The method according to claim 1, wherein the protective agent has the following formula

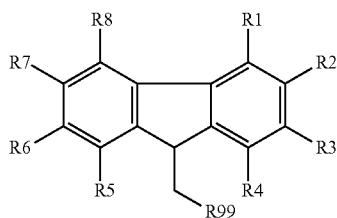

wherein R2 and R7 are SO$_3^-$ and R1, R3 to R6 and R8 are hydrogen, or R3 and R6 are SO$_3^-$ and R1, R2, R4, RS, R7 and R8 are hydrogen, and wherein R99 is selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups.

7. Protective agent according to claim 5, having the following formula

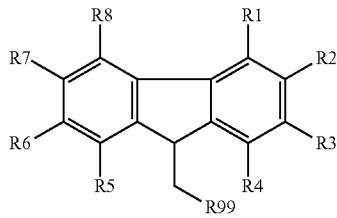

wherein R2 and R7 are SO$_3^-$ and R1, R3 to R6 and R8 are hydrogen, or R3 and R6 are SO$_3^-$ and R1, R2, R4, R5, R7 and R8 are hydrogen, and wherein R99 is selected from the group consisting of oxycarbonyl halogenide, oxycarbonyl O-succinimide, oxycarbonyl Oxyma ester, oxycarbonyl anhydride, halogenide, oxymethyl halogenide, hydroxide and thiol groups.

8. The method of claim 1, wherein the protective agent is used for forming protecting groups on functional groups on amino acids or peptides during water based peptide synthesis, and wherein the method comprises water-based reaction of a first amino acid or first peptide with an α-amine protected second amino acid or second peptide, wherein the second amino acid and/or second peptide is protected by protecting groups formed by the protective agent.

9. The method of claim 1, wherein the protective agent is used for forming protecting groups on functional groups on amino acids or peptides during water based peptide synthesis, and wherein the method further comprises deprotecting the functional groups and repeating the reaction and deprotection using further amino acids or peptides.

10. The method of claim 1, wherein said water based peptide synthesis is a peptide synthesis in a solvent limited to a solvent selected from the group consisting of water, alcohol and mixtures of water and alcohol; and wherein the protective agent enhances solubility of said second peptide or said second amino acid in said solvent.

11. The method of claim 10, further comprising, prior to reacting said second peptide or said second amino acid with said first peptide or said first amino acid in said solvent, protecting said at least one of said α-amino functional group of said second peptide or said second amino acid with said protective agent.

12. The method of claim 1, wherein the backbone structure comprises a 9-methylfluorene moiety.

13. A method of forming protecting groups on functional groups during water-based peptide synthesis, the method comprising using a protective agent,
wherein the protective agent comprises
a) a backbone structure,
b) at least two water-solubility enhancing functional groups and
c) at least one reactive group,
wherein the backbone structure comprises a moiety selected from the group consisting of 9-methylfluorene, and/or di- or triphenylmethane,
wherein the water-solubility enhancing functional groups are selected from SO$_3^-$, PO$_3^{2-}$, N(CH$_3$)$_2$, N(CH$_3$)$_3^+$, CN, OSO$_3^-$ ester, OPO$_3^{2-}$ ester and combinations thereof, and
wherein the water-solubility enhancing functional group and the reactive group are attached to the backbone structure via at least one covalent bond,
for protecting a functional group in a water-based reaction of a first amino acid or first peptide with an α-amine protected second amino acid or α-amine protected second peptide,
wherein said water based peptide synthesis is a peptide synthesis in a solvent limited to a solvent selected from the group consisting of water, alcohol and mixtures of water and alcohol; and wherein the protective agent enhances solubility of said second peptide or said second amino acid in said solvent, wherein using said protective agent for protecting a functional group in said water-based reaction comprises protecting said at least one of said α-amino functional group of said second peptide or said second amino acid with said protective agent prior to coupling said second peptide or said second amino acid with said first peptide or said first amino acid in said solvent.

* * * * *